United States Patent
He et al.

(10) Patent No.: US 8,032,209 B2
(45) Date of Patent: Oct. 4, 2011

(54) LOCALIZING NEURAL SOURCES IN A BRAIN

(75) Inventors: Bin He, Arden Hills, MN (US); Xiaoling Xu, Boothwyn, PA (US); Bobby Xu, Boothwyn, PA (US)

(73) Assignees: Regents of the University of Minnesota, St. Paul, MN (US); Board of Trustees of the University of Illinois, Urbana, IL (US)

( * ) Notice: Subject to any disclaimer, the term of this patent is extended or adjusted under 35 U.S.C. 154(b) by 1241 days.

(21) Appl. No.: 11/372,225

(22) Filed: Mar. 9, 2006

(65) Prior Publication Data
US 2006/0251303 A1    Nov. 9, 2006

Related U.S. Application Data

(63) Continuation of application No. PCT/US2004/029725, filed on Sep. 10, 2004.

(60) Provisional application No. 60/502,040, filed on Sep. 11, 2003.

(51) Int. Cl.
*A61B 5/04* (2006.01)

(52) U.S. Cl. ...................................... 600/544
(58) Field of Classification Search ............... 600/544, 600/545
See application file for complete search history.

(56) References Cited

U.S. PATENT DOCUMENTS

| 5,263,488 A | 11/1993 | Van Veen et al. |
| 5,426,365 A | 6/1995 | Sekihara et al. |
| 5,687,724 A | 11/1997 | Jewett et al. |
| 5,701,909 A | 12/1997 | Amir et al. |
| 6,330,470 B1 | 12/2001 | Tucker et al. |

FOREIGN PATENT DOCUMENTS

| EP | 0449231 A1 | 10/1991 |
| EP | 0527482 A1 | 2/1993 |
| WO | WO-2005025416 A2 | 3/2005 |
| WO | WO-2005025416 A3 | 3/2005 |

OTHER PUBLICATIONS

Hoffman et al. ("Eigenspace Based Spatial-Spectrum Estimation for Multiple Beam Antennas") CH2847-2/90/0000-2671, 1990 IEEE.*

Mosher et al. ("EEG Source Localization and Imaging Using Multiple Signal Classification Approaches") Journal of Clinical Neurophysiology 16(3):225-238. 1999.*

Khosla, D., et al., "Spatio-Temporal EEG Source Localization Using Simultaed Annealing", *IEEE Transactions on Biomedical Engineering*, 44(11), IEEE 1997,(Nov. 1997),1075-1091.

Mosher, J. C., et al., "Multiple Dipole Modeling and Localization from Spatio-Temporal MEG Data", *IEEE Transactions on Biomedical Engineering*, 39 (6), IEEE 1992,(Jun. 1,1992),541-557.

(Continued)

*Primary Examiner* — Patricia Mallari
*Assistant Examiner* — Christian Jang
(74) *Attorney, Agent, or Firm* — Schwegman, Lundberg & Woessner P.A.

(57) ABSTRACT

Described herein is a non-invasive determination of locations of neural activity in a brain. In particular, methods and systems have been developed that utilize a FINES algorithm for use in three-dimensional (3-D) dipole source localization to locate neural activity in a brain.

35 Claims, 12 Drawing Sheets

OTHER PUBLICATIONS

"International Application Serial No. PCT/US2004/029725, International Preliminary Report on Patentability dated Dec. 16, 2005", 12 pgs.

"International Application Serial No. PCT/US2004/029725, International Search Report mailed May 11, 2005", 3 pgs.

"International Application Serial No. PCT/US2004/029725, Written Opinion mailed May 9, 2005", 5 pgs.

Babiloni, F., et al., "High Resolution EEG: A New Model-Dependent spatial deblurring method using a realistically-shaped MR-constructed subject's head model", *Electroencephalography and Clinical Neurophysiology*, 102, (1997), 69-80.

Baillet, S., et al., "A Bayesian Approach to Introducing Anatomo-Functional Priors in the EEG/MEG Inverse Problem", *IEEE Transactions on Biomedical Engineering*, 44(5), (1997), 374-385.

Buckley, K. M., et al., "Spatial-Spectrum Estimation in a Location Sector", *IEEE Transactions on Acoustics, Speech and Signal Processing*, .38(11), (1990), 1842-1852.

Cooper, R., et al. (editors), EEG Technology, 3$^{rd}$ Edition, Chapters 1 & 9, (1980), 1-14, 231-314.

Cuffin, B. N., "A Method for Localizing EEG Sources in Realistic Head Models", *IEEE Transactions on Biomedical Engineering*, 42(1), (1995), 68-71.

Cuffin, B. N., "EEG Localization Accuracy Improvements Using Realistically Shaped Head Models", *IEEE Transactions on Biomedical Engineering*, 43(3), (1996), 299-303.

Cuffin, B. N., et al., "Effects of Head Shape on EEG's and MEG's", *IEEE Transactions.on Biomedical Engineering*, 37(1), (1990), 44-52.

Dale, A. M., et al., "Improving Localization of Cortical Activity by Combining EEG and MEG with MRI Cortical Surface Reconstruction: A Linear Approach", *Journal of Cognitive Neuroscience*, 5, (1993), 162-176.

Ding, L., et al., "Reduced Spatially Correlated Noise Influence using Subspace Source Localization Method FINES", *Proceedings of the 26th Annual Conference of the IEEE EMBS*, (Sep. 1-5, 2004, San Francisco, CA), (2004), 4393-4396.

Fuchs, M., et al., "Linear and Nonlinear Current Density Reconstructions", *Journal of Clinical Neurophysiology*, 16(3), (1999), 267-295.

Gevins, A., et al., "High resolution EEG: 124-channel recording, spatial deblurring and MRI integration methods", *Electroencephalography and clinical Neurophysiology*, 90, (1994), 337-358.

Gevins, A., "The future of electroencephalography in assessing neurocognitive functioning", *Electroencephalography and clinical Neurophysiology*, 106, (1998), 165-172.

Golub, G. H., et. al., *Matrix Computations*, vol. 3 of John Hopkins Series in the Mathematical Sciences, (1983), 428-431.

Gorodnitsky, I. F., et al., "Neuromagnetic source imaging with FOCUSS: a recursive weighted minimum norm algorithm", *Electroencephalography and clinical Neurophysiology*, 95, (1995), 231-251.

Hämäläinen, M. S., et al., "Realistic Conductivity Geometry Model of the Human Head for Interpretation of Neuromagnetic Data", *IEEE Transactions on Biomedical Engineering*, 36(2), (1989), 165-171.

He, B., et al., "A Cortical Potential Imaging Analysis of the P300 and Novelty P3 Components", *Human Brain Mapping*, 12, (2001), 120-130.

He, B., et al., "Boundary Element Method-Based Cortical Potential Imaging of Somatosensory Evoked Potentials Using Subjects' Magnetic Resonance Images", *NeuroImage*, 16, (2002), 564.576.

He, B., et al., "Electric Dipole Tracing in the Brain by Means of the Boundary Element Method and Its Accuracy", *IEEE Transactions on Biomedical Engineering*, vol. BME-34, No. 6, (1987), 406-414.

He, B., et al., "Equivalent dipole estimation of spontaneous EEG alpha activity: two-moving dipole approach", *Medical & Biological Engineering & Computing*, 30, (1992), 324-332.

He, B., et al., "Estimating Cortical Potentials from Scalp EEG's in a Realistically Shaped Inhomogeneous Head Model by Means of the Boundary Element Method", *IEEE Transactions on Biomedical Engineering*, 46(10), (1999), 1264-1268.

He, B., et al., "High-Resolution Spatio-Temporal Functional Neuroimaging of Brain Activity", *Critical Reviews™ in Biomedical Engineering*, 30(4-6), (2002), 283-306.

Kosugi, Y., et al., "Estimation of intra-cranial neural activities by means of regularized neural-network-based inversion techniques", *Neurological Research*, 23, (2001), 435-446.

Leahy, R. M., et al., "A study of dipole localization accuracy for MEG and EEG using a human skull phantom", *Electroencephalography and clinical Neurophysiology*, 107, (1998), 159-173.

Mosher, J. C., et al., "Source Localization Using Recursively Applied and Projected (RAP) Music", *IEEE Transactions on Signal Processing*, 47(2), (1999), 332-340.

Ni, Y., et al., "EEG Source Analysis of Motor Potentials Induced by Fast Repetitive Unilateral Finger Movement", *Proceedings of the 1st International IEEE EMBS Conference on Neural Engineering*, (Mar. 20-22, 2003, Capri Island, Italy), (2003), 541-544.

Rush, S., et al., "Current Distribution in the Brain From Surface Electrodes", *Anesthesia.and Analgesia,* 47(6), (1968), 717-723.

Scherg, M., et al., "Two Bilateral Sources of the Late AEP as Identified by a Spatio-Temporal Dipole Model", *Electroencephalography and clinical Neurophysiology*, 62, (1985), 32-44.

Schmidt, R. O., "Multiple Emitter Location and Signal Parameter Estimation", *IEEE Transactions on Antennas and Propagation*, vol. AP-34, No. 3, (first published in the Proceedings of the RADC Spectrum Estimation Workshop, held in Oct. 1979), (1986), 276-280.

Sekihara, K., et al., "Average-Intensity Reconstruction and Wiener Reconstruction of Bioelectric Current Distribution Based on Its Estimated Covariance Matrix", *IEEE Transactions on Biomedical Engineering*, 42(2), (1995), 149-157.

Sekihara, K., et al., "Noise Covariance Incorporated MEG-MUSIC Algorithm: A Method for Multiple-Dipole Estimation Tolerant of the Influence of Background Brain Activity", *IEEE Transactions on Biomedical Engineering*, 44(9), (1997), 839-847.

Strang, G., *Linear Algebra and its Applications*, (3rd Edition), Chapter 6, Harcourt, Brace, Jovanovich, San Diego, CA, (1988), 322-360.

Wang, Y., et al., "A Computer Simulation Study of Cortical Imaging from Scalp Potentials", *IEEE Transactions on Biomedical Engineering*, 45(6), (1998), 724-735.

Wood, C. C., "Application of Dipole Localization Methods to Source Identification of Human Evoked Potentials", *Annuals New York Academy of Sciences*, 388, (1982), 139-155.

Xu, X.-L., et al., "An alternative subspace approach to EEG dipole source localization", *Physics in Medicine and Biology*, 49, (2004), 327-343.

Xu, X.-L., et al., "Bias and Variance of Direction-of-Arrival Estimates from MUSIC, MIN-NORM, and FINE", *IEEE Transactions on Signal Processing*, 42(7), (1994), 1812-1816.

Xu,, X.-L., et al., "Bias Analysis of the MUSIC Location Estimator", *IEEE Transactions on Signal Processing*, 40(10), (1992), 2559-2569.

Zhang, Z., et al., "DSL and MUSIC Under Model Misspecification and Noise-Conditions", *Brain Topography*, 7(2), (1994), 151-161.

* cited by examiner

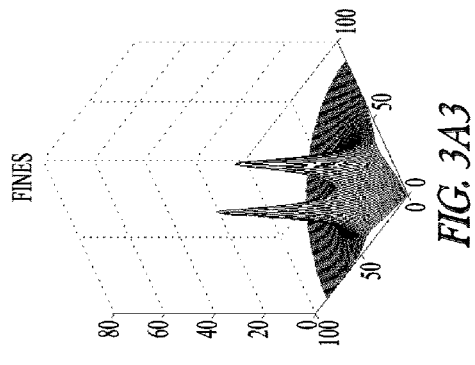
*FIG. 3A1*
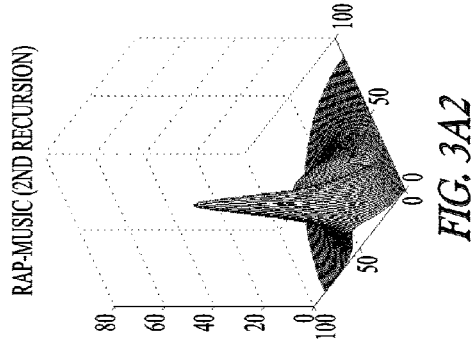
*FIG. 3A2*
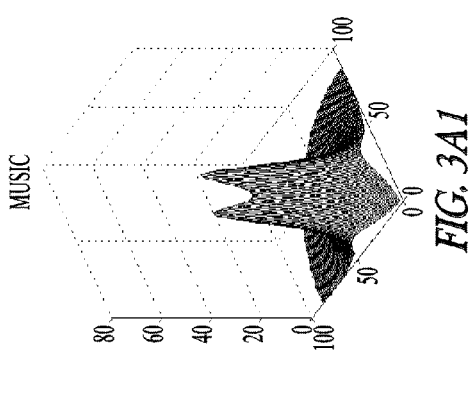
*FIG. 3A3*
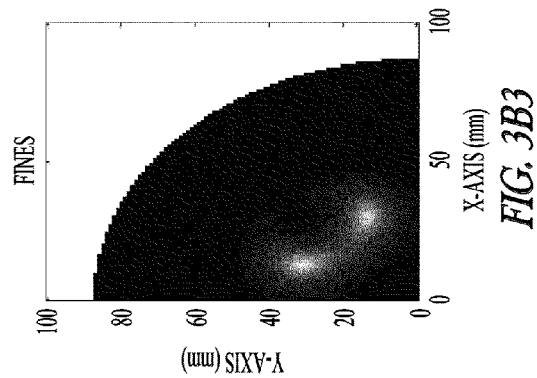
*FIG. 3B1*
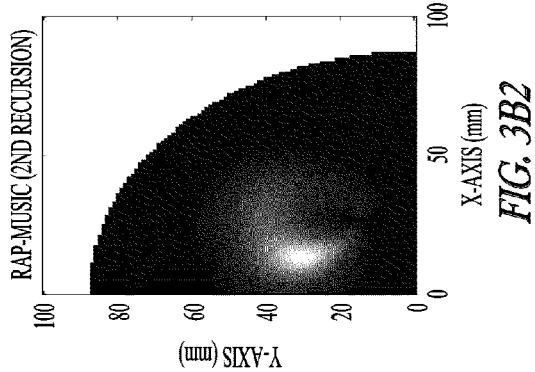
*FIG. 3B2*
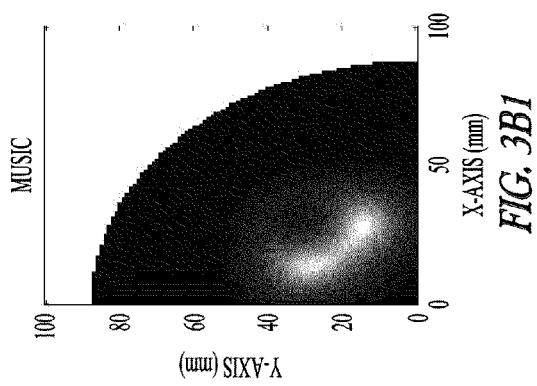
*FIG. 3B3*

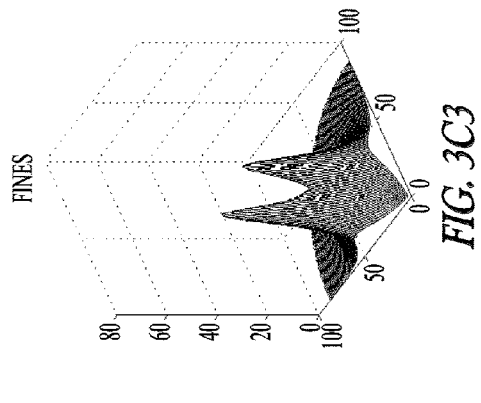
*FIG. 3C1* MUSIC
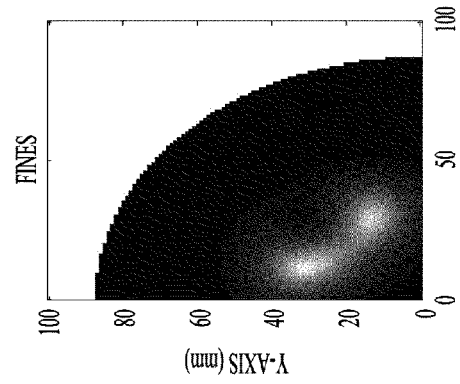 
*FIG. 3C2* RAP-MUSIC (2ND RECURSION)
*FIG. 3C3* FINES
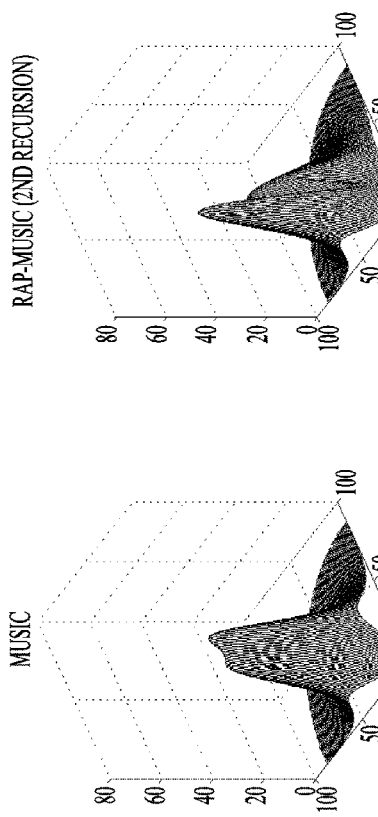
*FIG. 3D1* MUSIC
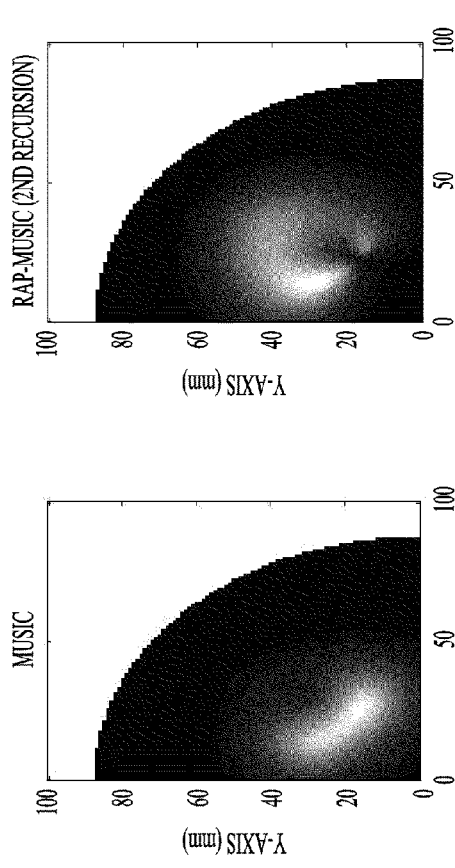
*FIG. 3D2* RAP-MUSIC (2ND RECURSION)
*FIG. 3D3* FINES

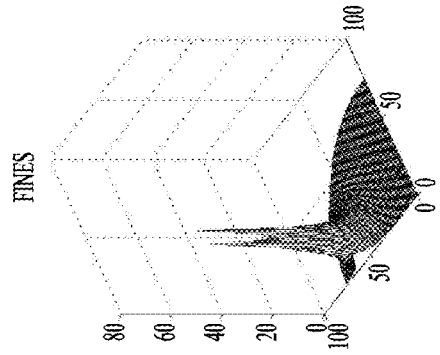
FIG. 4A1 MUSIC
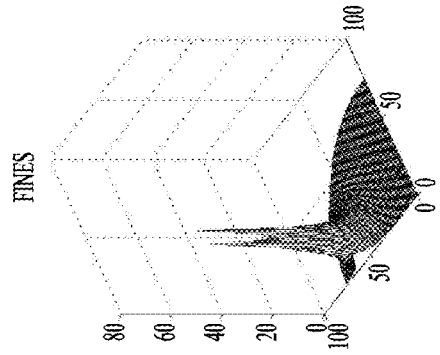
FIG. 4A2 RAP-MUSIC (2ND RECURSION)
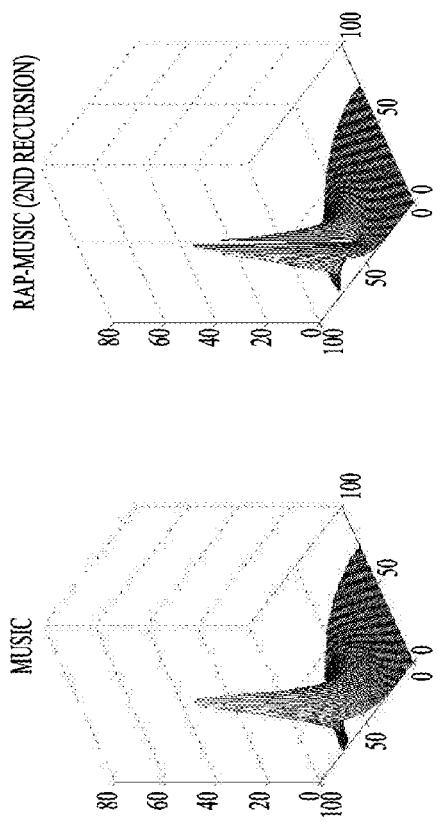
FIG. 4A3 FINES
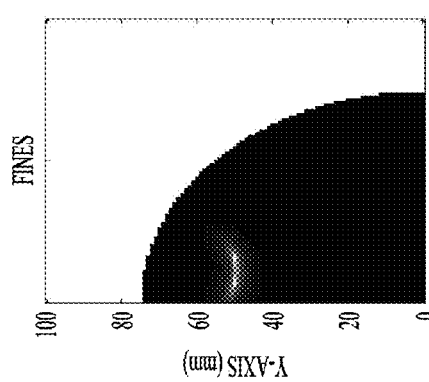
FIG. 4A4 MUSIC
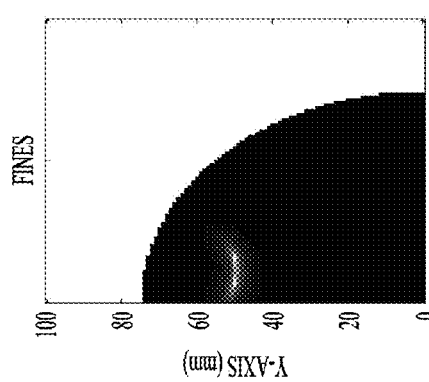
FIG. 4A5 RAP-MUSIC (2ND RECURSION)
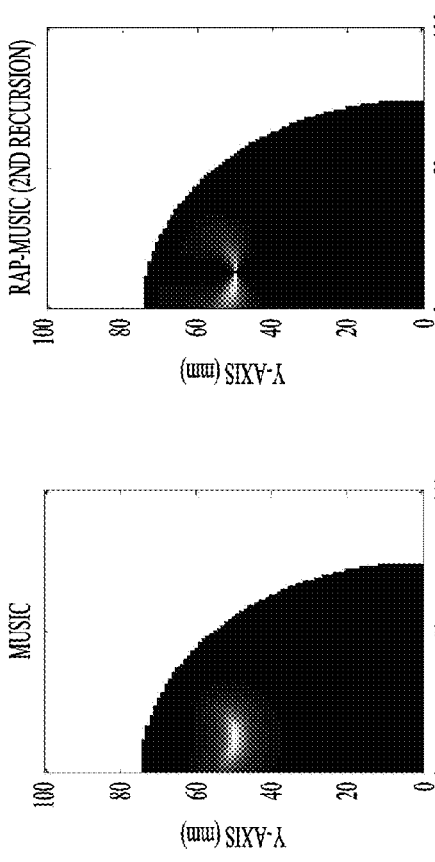
FIG. 4A6 FINES

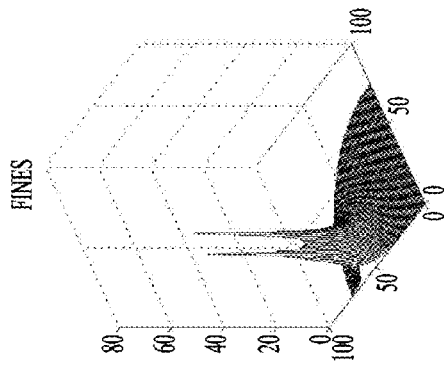
*FIG. 4B1* MUSIC
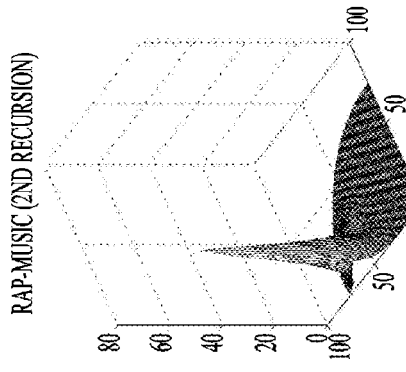
*FIG. 4B2* RAP-MUSIC (2ND RECURSION)
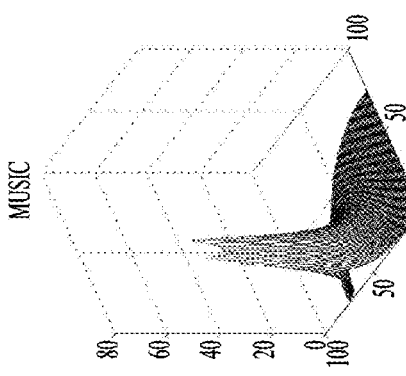
*FIG. 4B3* FINES
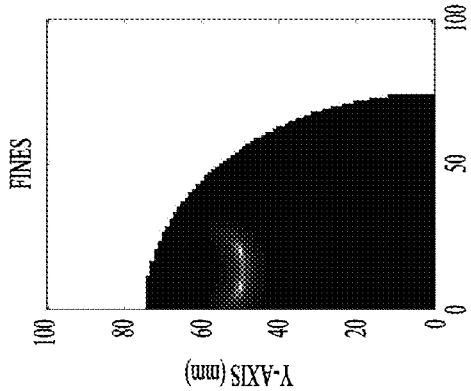
*FIG. 4B4* MUSIC
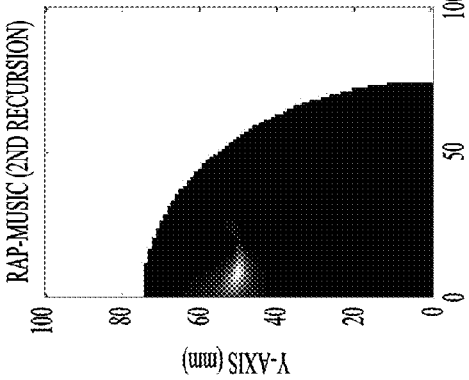
*FIG. 4B5* RAP-MUSIC (2ND RECURSION)
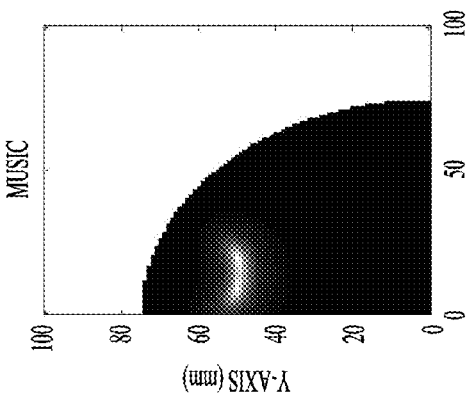
*FIG. 4B6* FINES

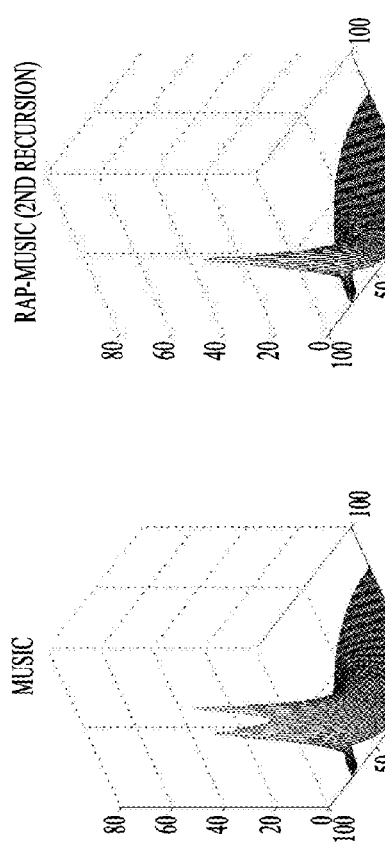
FIG. 4C1  FIG. 4C2  FIG. 4C3
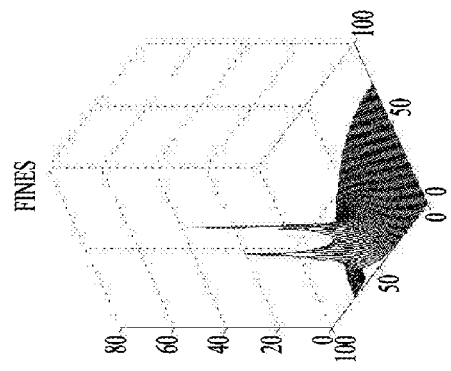
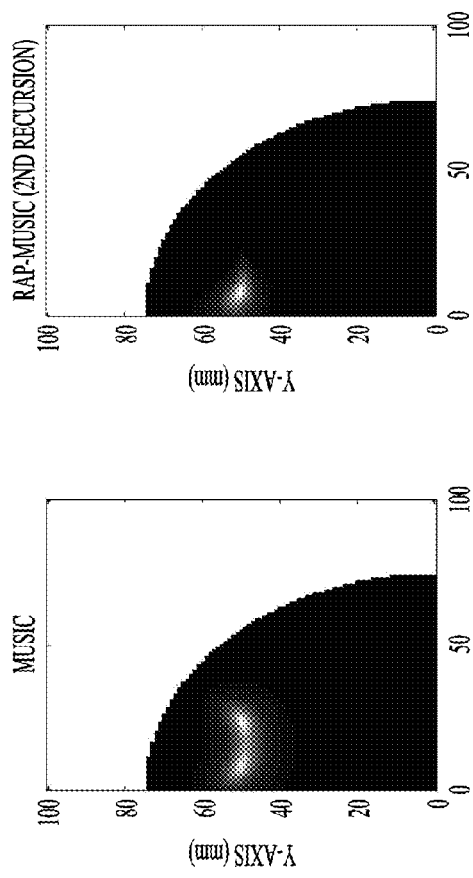
FIG. 4C4  FIG. 4C5  FIG. 4C6
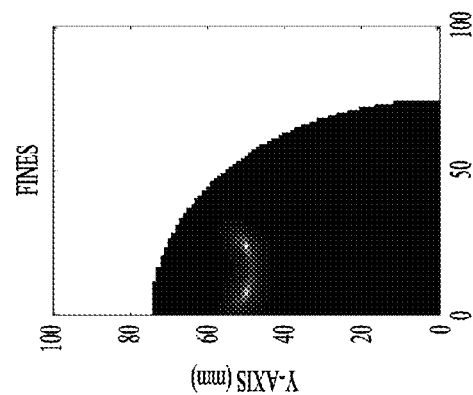

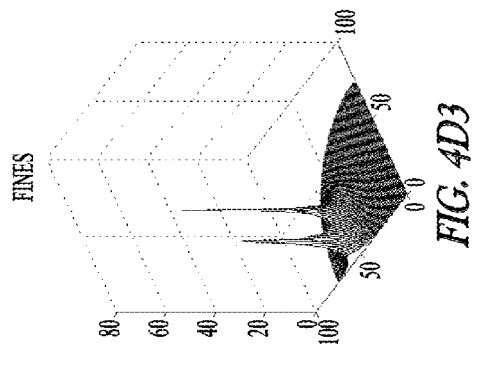
FIG. 4D3
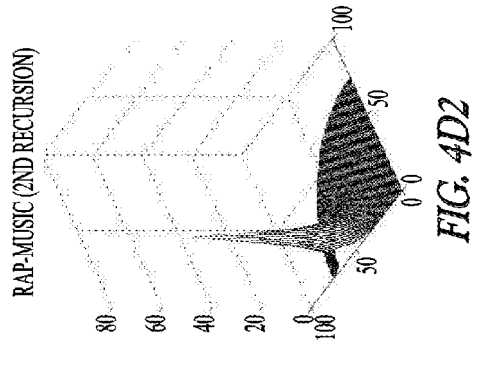
FIG. 4D2
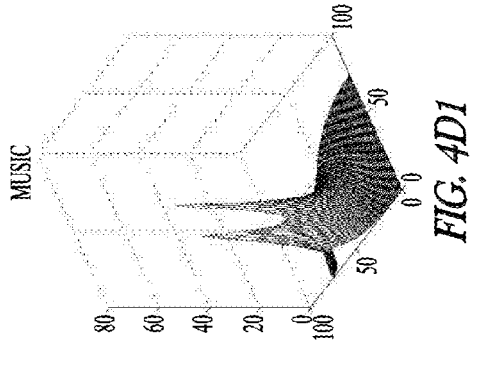
FIG. 4D1
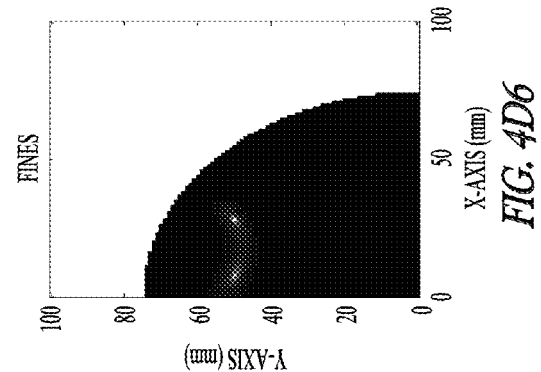
FIG. 4D6
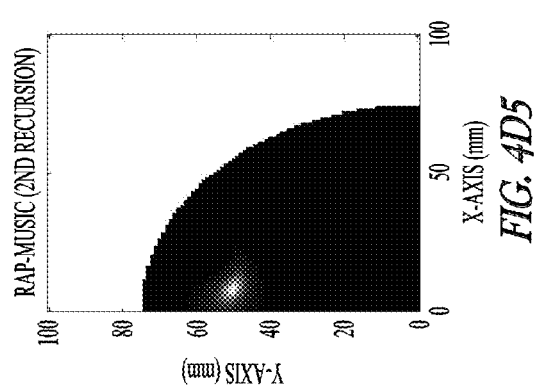
FIG. 4D5
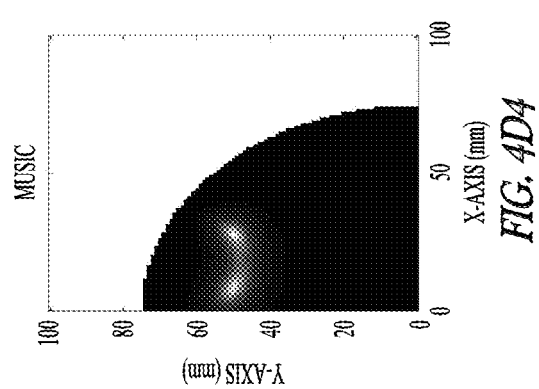
FIG. 4D4

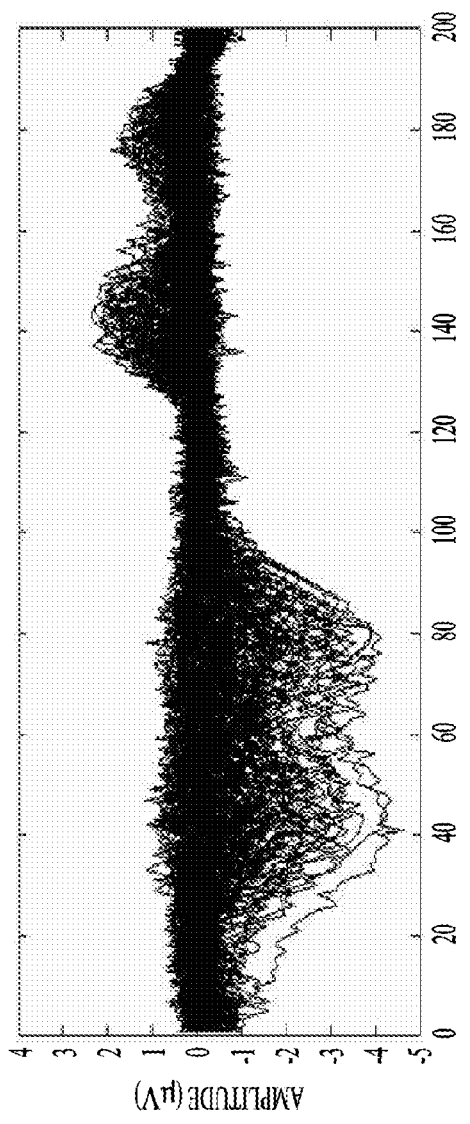
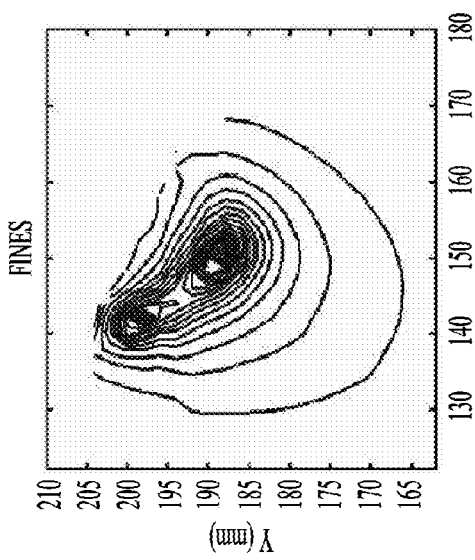
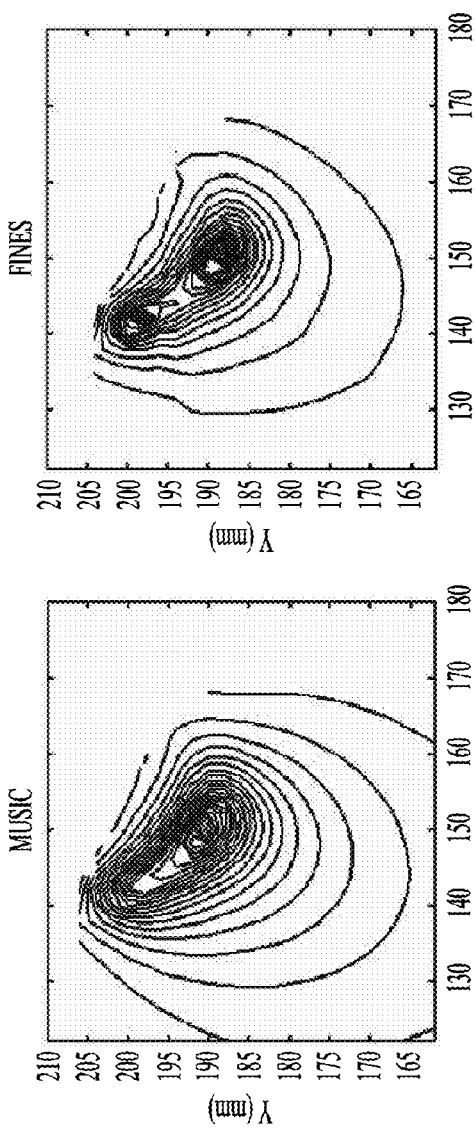
FIG. 5A
FIG. 5B
FIG. 5C

LOCALIZING NEURAL SOURCES IN A BRAIN

CLAIM OF PRIORITY

This application is a continuation under 35 U.S.C. 111(a) of International Application No. PCT/US2004/029725 filed Sep. 10, 2004 and published in English as WO 2005/025416 A2 on Mar. 24, 2005, which claims the benefit of priority, under 35 U.S.C. §119(e), to U.S. Provisional Patent Application Ser. No. 60/502,040, filed on Sep. 11, 2003, which is herein incorporated by reference.

STATEMENT REGARDING FEDERALLY SPONSORED RESEARCH

This invention was made with Government support under RO1EB00178 awarded by the National Institutes of Health and support under BES-0201939, BES-0218736, BES-0411480, and BES-0411898, awarded by the National Science Foundation. The Government has certain rights in this invention.

FIELD OF THE SUBJECT MATTER

The subject matter of the present document relates to the non-invasive determination of locations of neural activity in a brain.

BACKGROUND

Electroencephalography (EEG) and magnetoencephalogray (MEG) are non-invasive techniques used to study neural activities (Cooper et al. 1980; Genvins 1998; He and Lian 2002). One important application of EEG and MEG is source localization, i.e., the determination of locations of electrical activity in the brain from the EEG or MEG signals. Such source mapping plays an important role in localizing the origin(s) of neurological disorders such as epilepsy.

A problem in localizing sources is that a unique relationship may not exist between the recorded EEG or MEG signals and the neural source(s). Therefore, different source localization models have been created. One category of source models uses equivalent current dipole models to represent well-localized activated neural sources (Wood 1982; Scherg and von Cramon 1985; He et al. 1987; Mosher et al. 1992; Cuffin 1995).

Among the dipole source localization algorithms are the subspace-based methods (see Mosher et al. 1992; and Mosher and Leahy 1999). In principle, subspace-based methods find peak locations of their cost functions as source locations by employing certain projections onto the estimated signal subspace, or alternatively, onto the estimated noise-only subspace (i.e., the orthogonal complement of the estimated signal subspace), which are obtained from the measured EEG or MEG data. The subspace methods that have been studied for MEG/EEG include classic MUSIC (MUltiple SIgnal Classification) and recursive types of MUSIC: e.g., R-MUSIC (Mosher and Leahy 1999) and RAP-MUSIC (Mosher and Leahy 1999). Unfortunately, MUSIC typically provides biased estimates when sources are weak or highly correlated (e.g., Xu and Buckley 1992).

Background noise is referred to as brain noise, which is generated by spontaneous brain activities that cannot be suppressed or reduced by recording systems. Because of the inner generation mechanism for the noise, its appearance on all channels of recording system is spatially correlated. In contrast, uncorrelated noise can be introduced through the recording electrodes. The localization accuracy and spatial resolvability of the MUSIC algorithm is decreased in the presence of spatially correlated brain noise. The noise covariance incorporation treatment of MUSIC algorithm in (Sekihara et al., 1997) is one possible way to deal with such problem, but the required noise covariance matrix is unknown in most cases or at best difficult to be estimated in many experimental conditions.

Accordingly, there is a need for a new method for improving the spatial resolution of source localization in the brain.

SUMMARY OF CERTAIN EMBODIMENTS

Methods and systems have been developed that utilize a FINES (FIrst priNciple vEctorS) algorithm for use in three-dimensional (3-D) dipole source localization to locate neural activity in a brain. Accordingly, provided herein is a system including: a storage unit configured to store data corresponding to electrical activity of a brain; a processor coupled to the storage unit and configured to execute a set of instructions to generate a location of at least one dipole source corresponding to the stored data, the location determined by an extreme of a cost function applied to a projection of a set of vectors, the set of vectors related to an array manifold associated with a selected region of the brain and the set of vectors spanning a first subspace determined by the stored data and a selected portion of a second subspace wherein the second subspace is orthogonal to the first subspace; and an output device for rendering a location of the at least one dipole source.

Also provided is a processor implemented method including: estimating a first subspace based on measured data for a brain; calculating a second subspace, wherein the second subspace is orthogonal to the first subspace; identifying a set of vectors of the second subspace, the vectors related to an array manifold associated with a selected region of the brain; applying a projection onto the set of vectors; and determining a location for each of at least one source based on a cost function of the projection for the selected region.

Also provided is a computer-readable medium having stored thereon a set of instructions executable by a processor to perform a method of identifying at least one source dipole in a brain including: receiving data based on sampled electrical activity of the brain for a period of time; dividing a volume of the brain into a number of regions; for each region, determining a subspace that is spanned by an array manifold corresponding to the region, the array manifold formed by a collection of gain matrices, the gain matrices determined by field responses corresponding to a plurality of sensors and a dipole disposed in the region; for a particular set of time samples of the data, forming a sample spatial correlation matrix; applying eigen-decomposition to the sample spatial correlation matrix to form an estimated noise-only subspace; for each region, identifying a set of vectors, wherein the set of vectors resides in the estimated noise-only subspace which is closest to the subspace spanned by the array manifold associated with the region; forming projections for each of a plurality of array response vectors associated with a plurality of locations within the brain and having a plurality of orientations; and identifying a location of at least one source dipole based on searching the projections across a location vector and an orientation vector wherein the location corresponds to a first predetermined feature of a cost function.

In accordance with certain embodiments, an imaging instrument for localizing neural electrical sources within the brain includes means for collecting biosignals over a part of a surface or volume, inside or outside of the head, means for localizing source dipoles within the brain using a subspace source localization method called FINES, means for displaying the estimated dipole source distribution over the three dimension of the brain, means for displaying the collected biosignals in both time domain and space domain together with the estimated source dipole distribution, and means for displaying the estimated electrical sources, together with other brain images including magnetic resonance imaging and computer tomography.

The positions of sensors and the geometry of the head and brain can also be determined using other imaging modalities, such as magnetic resonance imaging or computer tomography. The geometry information can be used to construct a realistic geometry inhomogeneous head model representing the conductive medium of the head. The gain matrix can be evaluated using this accurate representation of the head volume conductor. Regions of interest of the brain are then defined, and FINES vectors constructed.

Means and methods for aiding pre-surgical planning or surgical planning for epilepsy patients are also provided. The present subject matter will assist in identifying the epileptogenic foci, for example, in order to treat medically refratory epilepsy. In accordance with this aspect, the epileptogenic foci are estimated using the FINES approach from EEG and/or MEG signals collected in a patient during the interictal spikes, slow waves, or ictal spikes. In accordance with this aspect, a time-frequency signal processing approach can be used to determine the time period and frequency window for the source analysis of the ictal data. The time-frequency filtered ictal data of a patient are then fed into the FINES source localization procedure and dipole sources estimated. Such obtained dipole sources are used to guide the surgical resection of the epilepsy patients and to minimize damage to brain tissue that is otherwise healthy.

One aspect of the subject matter further relates to methods wherein scalp EEG signals are measured using electrodes, the electrode positions are determined, the head-brain geometry information is determined from magnetic resonance imaging or computer tomography imaging, brain dipole sources are estimated from scalp potentials and the head-brain geometry information using the FINES procedure, and displayed over the three dimensional brain, with or without displaying of other brain imaging results including magnetic resonance imaging.

Another aspect of the subject matter further relates to methods wherein magnetoencephalograms are measured using superconducting quantum interference device (SQUID) sensors or other sensors, the magnetic sensor positions are determined, the head-brain geometry information is determined from magnetic resonance imaging or computer tomography imaging, and brain dipole sources are estimated from magnetoencephalograms and the head-brain geometry information using the FINES procedure, and displayed over the three dimensional brain, with or without displaying of other brain imaging results including magnetic resonance imaging.

Another aspect further relates to methods wherein both electroencephalograms and magnetoencephalograms are measured using electrode sensors and/or SQUID and/or other magnetic sensors, the positions of the electrical and magnetic sensors are determined, the head-brain geometry information is determined from magnetic resonance imaging or computer tomography imaging, and brain dipole sources are estimated from electroencephalograms and/or magnetoencephalograms, as well as the head-brain geometry information using the FINES procedure, and displayed over the three dimensional volume of the brain, with or without displaying of other brain imaging results including magnetic resonance imaging.

Thus, the present subject matter provides a new method of localizing brain electrical sources in the three dimensional brain, using a novel subspace source localization algorithm called FINES. Thus, an important tool, aiding pre-surgical or surgical planning in epilepsy patients or patients with other neurological or psychiatric disorders, is presented herein.

BRIEF DESCRIPTION OF THE FIGURES

FIG. 3 depicts two-dimensional (2-D) mesh plots and images at z=20 mm of the three algorithms for simulation setting 1 with radial orientation. They represent the reciprocal of their minimization cost functions for MUSIC and for FINES, and the one used in the $2^{nd}$ recursion for RAP-MUSIC. FIG. 3A (including FIGS. 3A1, 3A2, and 3A3) and 3B (including FIGS. 3B1, 3B2, and 3B3): SNR=10 dB and $\rho=0.25$; FIG. 3C (including FIGS. 3C1, 3C2, and 3C3) and 3D (including FIGS. 3D1, 3D2, and 3D3): SNR=6 dB and $\rho=0.25$.

FIG. 4 depicts 2-D mesh plots and images at z=50 mm of the three algorithms for simulation setting 3, FIG. 4A (including FIGS. 4A1, 4A2, 4A3, 4A4, 4A5, and 4A6), case 1: dipole 1 was located at [8, 50, 50] mm, dipole 2 was located at [16, 50, 50] mm (the dipole separation was 8 mm); FIG. 4B (including FIGS. 4B1, 4B2, 4B3, 4B4, 4B5, and 4B6), case 2: dipole 1 was located at [8, 50, 50] mm, dipole 2 was located at [20, 50, 50] mm (the dipole separation was 12 mm); FIG. 4C (including FIGS. 4C1, 4C2, 4C3, 4C4, 4C5, and 4C6), case 3: dipole 1 was located at [8, 50, 50] mm, dipole 2 was located at [24, 50, 50] mm (the dipole separation was 16 mm); and FIG. 4D (including FIGS. 4D1, 4D2, 4D3, 4D4, 4D5, and 4D6), case 4: dipole 1 was located at [8, 50, 50] mm, dipole 2 was located at [28, 50, 50] mm (the dipole separation was 20 mm).

FIG. 5 (including FIGS. 5A, 5B, and 5C) depicts simulated two current dipole sources waveforms on 94 channels shown in the top plot (FIG. 5A). 2D contour plot of MUSIC estimate at a cross-section of the brain only shows one extreme point (bottom, left; FIG. 5B) and 2D contour plot of FINES estimate at the same cross-section of the brain shows two extreme points (bottom, right; FIG. 5C).

FIG. 6 (including FIGS. 6A, 6B, and 6C) depicts waveforms from 94 channel recordings of finger movement tasks (top.

DETAILED DESCRIPTION

Figure 1A:
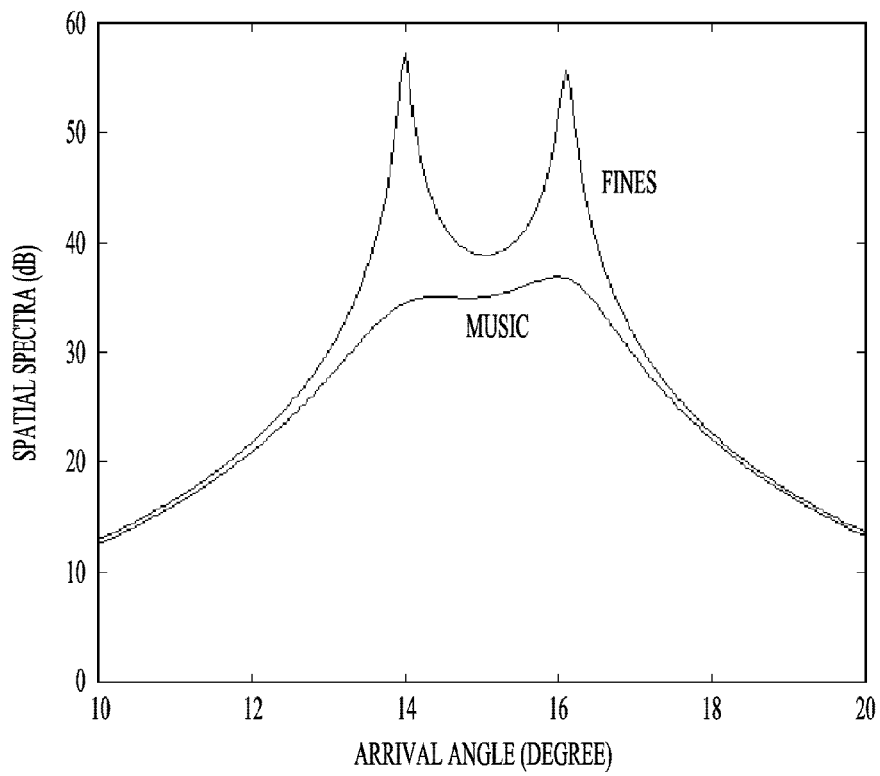
FIGS. 1A and 1B depict 1-D spatial spectra (values of their cost functions) of MUSIC, FINES and RAP-MUSIC. Two uncorrelated and equi-powered sources arrived from 14 and 16 degrees, array configuration was a standard linear array of 10 sensors, and the signal to noise ratio (SNR) was 18 dB. For FINES the region sector was 0-30 degree, and the number of FINES vectors was 2.

Methods and systems have been developed that utilize a FINES algorithm for use in 3-D dipole source localization to locate neural activity in a brain. Accordingly, provided herein is a system including: a storage unit configured to store data corresponding to electrical activity of a brain; a processor coupled to the storage unit and configured to execute a set of instructions to generate a location of at least one dipole source corresponding to the stored data, the location determined by an extreme of a cost function applied to a projection of a set of vectors, the set of vectors related to an array manifold associated with a selected region of the brain and the set of vectors spanning a first subspace determined by the stored data and a selected portion of a second subspace wherein the second subspace is orthogonal to the first subspace; and an output device for rendering a location of the at least one dipole source.

In some embodiments, the system further includes a plurality of sensors coupled to the storage unit. In some embodiments, at least one sensor of the plurality of sensors includes at least one of an electric field sensor and a magnetic field sensor.

In some embodiments, the output device includes at least one of a memory, a printer and a display. In some embodiments, the output device is configured to generate a three-dimensional image.

Also provided is a processor implemented method including: estimating a first subspace based on measured data for a brain; calculating a second subspace, wherein the second subspace is orthogonal to the first subspace; identifying a set of vectors of the second subspace, the vectors related to an array manifold associated with a selected region of the brain; applying a projection onto the set of vectors; and determining a location for each of at least one source based on a cost function of the projection for the selected region.

In some embodiments, the set of vectors have minimum principal angles to the array manifold. In some embodiments, the method further includes calculating the array manifold based on a collection of gain matrices corresponding to the at least one source for the selected region, wherein the gain matrices are based on field responses corresponding to the measured data.

In some embodiments, applying the projection onto the set of vectors includes calculating a projection of an array response vector onto the second subspace, where the array response vector is a response to a unit dipole having a predetermined location and a predetermined orientation as measured by a sensor array about the brain. In some embodiments, the set of vectors have minimum principal angles to the array manifold. In some embodiments, determining the location includes identifying a predetermined extrema of the cost function.

In some embodiments, estimating the first subspace includes processing at least one of electroencephalography data and magnetoencephalography data. In some embodiments, estimating the first subspace includes receiving signals corresponding to electrical activity of the brain. In some embodiments, receiving signals includes receiving signals from a plurality of sensors disposed about the brain.

In some embodiments, the first subspace includes a signal-only subspace. In some embodiments, the second subspace includes a noise-only subspace.

In some embodiments, the method further includes generating a three dimensional image depicting the location of each of the at least one source relative to the brain. In some embodiments, the method further includes generating at least one cross-sectional image or plot depicting the location for each of at least one source relative to the brain. In some embodiments, generating the three dimensional image includes generating an image using at least one of magnetic resonance data, computerized tomography data, x-ray data and ultrasonic data. In some embodiments, the set of vectors spans the second subspace.

In some embodiments, the method further includes generating a sample spatial correlation matrix based on averaging outer products of a number of time samples and wherein the set of vectors includes a number of eigenvectors corresponding to eigenvalues of the sample spatial correlation matrix. In some embodiments, the number of eigenvectors corresponds to a difference between a number of sensors and a number of dipole sources. In some embodiments, calculating the second subspace includes using a second set of vectors corresponding to a number of largest eigenvalues of the sample spatial correlation matrix.

Also provided is a computer-readable medium having stored thereon a set of instructions executable by a processor to perform a method of identifying at least one source dipole in a brain including: receiving data based on sampled electrical activity of the brain for a period of time; dividing a volume of the brain into a number of regions; for each region, determining a subspace that is spanned by an array manifold corresponding to the region, the array manifold formed by a collection of gain matrices, the gain matrices determined by field responses corresponding to a plurality of sensors and a dipole disposed in the region; for a particular set of time samples of the data, forming a sample spatial correlation matrix; applying eigen-decomposition to the sample spatial correlation matrix to form an estimated noise-only subspace; for each region, identifying a set of vectors, wherein the set of vectors resides in the estimated noise-only subspace which is closest to the subspace spanned by the array manifold associated with the region; forming projections for each of a plurality of array response vectors associated with a plurality of locations within the brain and having a plurality of orientations; and identifying a location of at least one source dipole based on searching the projections across a location vector and an orientation vector wherein the location corresponds to a first predetermined feature of a cost function.

In some embodiments, closeness is measured in the sense of a principal angle. In some embodiments, receiving data includes receiving at least one of magnetoencephalography data and electroencephalography data. In some embodiments, receiving data includes receiving data using a plurality of electrical electrode sensors disposed about the brain. In some embodiments, receiving data includes receiving data using a plurality of magnetic sensors disposed about the brain.

In some embodiments, the computer-readable medium further includes identifying an orientation of the at least one source dipole based on searching the projections across a location vector and an orientation vector wherein the orientation corresponds to a second predetermined feature of the cost function.

In some embodiments, the first predetermined feature includes at least one of a minima and a maxima of the cost function. In some embodiments, identifying the set of vectors includes determining principal angles. In some embodiments, receiving data based on sampled electrical activity includes receiving location data for at least one of a plurality of sensors.

In some embodiments, the computer-readable medium further includes determining brain or head geometry using at least one of magnetic resonance and computer tomography. In some embodiments, the computer-readable medium further includes calculating the array response vectors based on at least one of a boundary element method, a finite element method and a finite difference method.

In some embodiments, a time-frequency analysis is performed on the data to extract significant components.

This innovation in the three dimensional brain source localization by using the FINES approach advances state of the art in brain source localization and aids presurgical and/or surgical planning of epilepsy surgery.

Thus, presented herein is a new approach to 3-D dipole source localization by adapting a subspace algorithm called FINES. FINES is one of the CLOSEST algorithms. The CLOSEST approach identifies and employs projections onto a particular vector or a set of vectors in the estimated noise-only subspace instead of the entire estimated noise-only subspace. The subspace spanned by this vector set is, in some sense, closest to the subspace spanned by the array manifold associated with a particular region of interest.

Neural sources, e.g., well-localized activated neural sources, are modeled with equivalent current dipoles. Therefore, determining the locations of neural sources becomes the problem of estimating the locations of dipole sources. In estimating dipole source locations, the present subject matter employs the FINES technique, which uses projections onto a subspace spanned by a set of particular vectors (FINES vector set) in the estimated noise-only subspace. The subspace spanned by this vector set is, in the sense of principal angle, closest to the subspace spanned by the array manifold associated with a particular brain region.

By incorporating knowledge of the array manifold in identifying FINES vector sets in the estimated noise-only subspace for different brain regions, source locations can be determined with enhanced accuracy and spatial resolution, thus enhancing the capability of resolving closely-spaced neural sources and reducing estimation errors.

One embodiment provides a method of localization of neural electrical activities in the brain including the steps of collecting signals over a part of the head or over a part of a surface or volume out of the head using a plurality of sensors and a data acquisition unit, constructing a source dipole distribution representing the electrical activities of the brain, estimating the source dipole locations, employing the FINES technique, which uses projections onto a subspace spanned by a set of particular vectors (FINES vector set) in the estimated noise-only subspace, and displaying the estimated source dipole distributions within the three dimension space of the brain, with or without displaying simultaneously anatomic images of the brain as obtained from other imaging modalities such as magnetic resonance imaging.

In some embodiments, the estimated noise-only subspace is a subspace spanned by the set of eigenvectors corresponding to the K−p smallest eigenvalues of the sample spatial correlation matrix obtained by averaging the outer products of a number of time samples, where K is the number of electrodes and p is number of dipoles. In some embodiments, the estimated noise-only subspace is created using the set of eigenvectors corresponding to the p largest eigenvalues of the sample spatial correlation matrix, in the form of orthogonal complement of the subspace spanned by the p eigenvectors in the K dimensional space.

In some embodiments, the FINES vector set spans the subspace which is, in the sense of principal angle, closest to the subspace spanned by the array manifold associated with a particular brain region. In some embodiments, the "principal angle" is a principal angle between two subspaces. In some embodiments, the array manifold is the collection of gain matrices corresponding to a dipole while its location and orientation vary. In some embodiments, the array manifold associated with a particular brain region is the collection of gain matrices corresponding to a dipole while its location varies within the particular brain region and orientation varies with or without restriction.

In some embodiments, the projection is the projection of the K×1 array response vector onto the subspace spanned by the FINES vector set, where the array response vector is the electrode array's response to a unit dipole at a given location and with given orientation.

In some embodiments, the algorithm of determining the locations of dipole sources contains the following steps:
  a. Divide the brain volume into a number of regions.
  b. For each given region, determine a subspace that is essentially spanned by the array manifold corresponding to the region.
  c. For given time samples of EEG and/or MEG measurement, form the sample spatial correlation matrix.
  d. By applying eigen-decomposition to the sample spatial correlation matrix, form the estimated noise-only subspace.
  e. For each region, identify a set of FINES vectors.
  f. Form projections for array response vectors associated with all locations within the brain and all possible orientations.
  g. Search minima of the projections across the location vector and orientation vector, and the estimates of p dipoles' locations are corresponding to the location of the p minima of the projections.

In some embodiments, the searching for dipole location and searching for dipole orientation can be done in two separate sub-steps of step g.

In some embodiments, MEG measurements are used. In some embodiments, EEG measurements are used. In some embodiments, a combination of EEG and MEG measurements are used.

In some embodiments, the minimization procedure can be replaced by maximization procedures by using the reciprocal or negative of the cost function, or other similar techniques. In some embodiments, other closeness measure than the principal angle can be used to form the FINES vector set.

In some embodiments, the signals are collected using an array of electrical electrode sensors over the scalp or the surface of the brain. In some embodiments, the signals are collected using an array of magnetic sensors out of the head. In some embodiments, the signals are collected using a combination of an array of electrical electrode sensors over the scalp or the surface of the brain and an array of magnetic sensors out of the head. In some embodiments, the locations of the sensors are determined and used in the FINES source localization.

In some embodiments, the geometry of the head and/or brain are determined by, for example, magnetic resonance imaging or computer tomography, and realistic geometry head model is constructed using the boundary element method, the finite element method, the finite difference method, or other numerical techniques, for the computation of the array response vectors.

In some embodiments, the time-frequency analysis is performed on the said collected signals to extract significant components of interest for the FINES analysis.

In some embodiments, the FINES source localization results are used alone or used in combination with other source localization procedures to aid pre-surgical planning in epilepsy patients. In some embodiments, the FINES source localization results are used alone or used in combination with other source localization procedures to aid surgical planning, for example, for epilepsy patients.

Also provided is an apparatus for localization of electrical activities in the brain, including a plurality of sensors for detecting signals over a part of the scalp or over a part of a surface or volume out of the head, means for collecting the detected signals, means for estimating the source dipole locations, employing FINES technique, which uses projections onto a subspace spanned by a set of particular vectors (FINES vector set) in the estimated noise-only subspace, where the subspace spanned by this vector set is, in the sense of principal angle, closest to the subspace spanned by the array manifold associated with a particular brain region, and means for displaying the estimated source dipole distributions within the three dimension space of the brain.

In some embodiments, the apparatus receives electrical signals from electrodes that are distributed at known locations around a head, e.g., of a human. The received analog signals, after being amplified and filtered, are converted to digital data. The digital data are then processed with a source localization technique called FINES to determine the locations of the neural sources. The estimated source locations can be displayed, achieved or transmitted, e.g., to a different place.

In certain embodiments, a realistic geometry inhomogeneous head model is used to represent the head volume conductor. The head model is constructed from, for example, the MRI and/or CT scans of the subjects and is segmented and digitized. The boundary element meshes are built using triangle elements covering the scalp, the skull, and the cortical surfaces, etc. to form a multi-layer realistic geometry boundary element model of the head volume conductor. The boundary element algorithm is used to compute the gain matrix and used to form the FINES vectors for FINES analysis.

In accordance with another embodiment, the finite element method is used to construct the head volume conductor model. The head model is constructed from the MRI and/or CT scans of the subject and is segmented and digitized. The finite elements are built for the entire head volume conductor model including the scalp, the skull, and the brain region. The anisotropic and inhomegeneous characteristics of the head volume conductor can optionally be incorporated into such finite element model of the head. The finite element algorithm is used to compute the gain matrix and used to form the FINES vectors for FINES analysis.

In accordance with another embodiment, the finite difference method is used to construct the head volume conductor model. The head model is constructed from the MRI and/or CT scans of the subject and is segmented and digitized. The finite difference elements are built for the entire head volume conductor model including the scalp, the skull, and the brain region. The finite difference algorithm is used to compute the gain matrix and used to form the FINES vectors for FINES analysis.

Thus, as described herein, using FINES for EEG and/or MEG source localization by employing projections onto a particular set of vectors in the noise-only subspace instead of entire noise-only subspace obtains a smaller estimation bias and better spatial resolution for closely spaced sources (Xu et al., 2004).

The subject matter will now be illustrated by the following non-limiting Examples.

Example 1

The FINES Technique

Assume $f(t_n)$ denotes the EEG measurement vector, which is the collection of all electrode output at the time $t_n$. If the number of electrodes is K, then $f(t_n)$ is a K×1 vector. Dipole source localization estimates the dipole locations from given N time samples: $\{f(t_n); n=1, \ldots, N\}$.

Let $\hat{R}_f$ denote the sample correlation matrix of $R_f$, obtained by averaging the outer products of N time samples: $\{f(t_n); n=1, \ldots, N\}$, i.e., $$\hat{R}_f = \frac{1}{N} \sum_{n=1}^{N} f(n) f^T(n). \qquad \text{(Equation A)}$$

Assume $\{\hat{\lambda}_i; i=1, 2, \ldots, K; \hat{\lambda}_i \geq \hat{\lambda}_{i+1}\}$ and $\{\hat{e}_i; i=1, 2, \ldots, K\}$ to be the ordered eigenvalues and their corresponding normalized eigenvectors of $\hat{R}_f$. If the number of detected dipoles is p, the collection of the first p eigenvectors is denoted by $\hat{E}_s$, a K×p matrix, and the collection of the rest eigenvectors by $\hat{E}_n$, a K×(K−p) matrix. That is, $$\hat{E}_s = [\hat{e}_1, \hat{e}_2, \ldots, \hat{e}_p], \qquad \text{(Equation B)}$$

and $$\hat{E}_n = [\hat{e}_{p+1}, \hat{e}_{p+2}, \ldots, \hat{e}_K]. \qquad \text{(Equation C)}$$

The column space of $\hat{E}_s$ is the estimated signal subspace and the column space of $\hat{E}_n$ is the estimated noise-only subspace.

FINES identifies a low-dimensional subspace, i.e., the FINES vector set that spans this low-dimensional subspace, in the estimated noise-only subspace that has the minimum principal angle to the subspace spanned by the section of the array manifold corresponding to a selected brain region. The array manifold represents a collection of the gain matrices when dipole location $\vec{l}$ varies over a selected region:

$$\Gamma = \{G(\vec{l}) | \vec{l} \in \Theta\}, \qquad \text{(Equation D)}$$

where $G(\vec{l})$ is the gain matrix (K×3) corresponding to three x, y, z unit-dipoles located at $\vec{l}$, and $\Theta$ represents the selected region. FINES employs this vector set to form a projection operator in searching dipole locations within the selected region. To search dipole locations over the entire brain, different sets of FINES vectors are used to form projection operators for different brain regions.

Below are the steps of the FINES technique for 3-dimensional dipole source localization:

1. Divide the brain volume into a number of regions.
2. For the $k^{th}$ region $\Theta_k$, determine a subspace that essentially spans the array manifold corresponding to the region, i.e., $\{G(\vec{l}): \vec{l} \in \Theta_k\}$ where $\vec{l} = [x, y, z]^T$. This can be achieved through the following steps:
   a. Form a spatially extended source representation matrix for the selected brain region $\Theta_k$:

$$R_{\Theta_k} = \int_{\Theta_k} w(\vec{l}) \cdot G(\vec{l}) G^T(\vec{l}) d\vec{l}, \qquad \text{(Equation E)}$$

where $w(\vec{l})$ is a weighting function that can include a priori information and additional information about array configuration and characteristics of electrodes.

b. Perform an eigen-decomposition on $R_{\Theta_k}$ with eigenvalues in nonincreasing order (i.e., the first eigenvalue is the largest and the last eigenvalue is the smallest). Because $R_{\Theta_k}$ is typically of low rank, there are only a few significant eigenvalues.

c. Select the first $D_{\Theta_k}$ eigen-vectors that are associated with the $D_{\Theta k}$ largest eigenvalues of $R_{\Theta_k}$ and form:

$$V_{\Theta_k} = [v_1, v_2, \ldots, v_{D_{\Theta k}}].\quad\text{(Equation F)}$$

$D_{\Theta_k}$ can be determined via various criteria. One of them is choosing $D_{\Theta_k}$ such that the summation of the first $D_{\Theta_k}$ eigenvalues is not less than, e.g., 99% of the summation of all eigenvalues. This threshold can be a different percentage rather than 99% if desired.

3. Repeat step 2 for all regions. All $V_\Theta$'s can be pre-generated and stored, if desired.
4. For given time samples of EEG and/or MEG measurement, form sample correlation matrix $\hat{R}_f$ as Equation A.
5. By applying an eigen-decomposition to $\hat{R}_f$, generate the estimated noise-only subspace, i.e., the eigenvector matrix $\hat{E}_n$.
6. For the $k^{th}$ region $\Theta_k$, identify a set of $D_{\Theta_k}$ FINES vectors from the given $\hat{E}_n$, which is closest to the range of $V_{\Theta_k}$ in the sense of principal angle. Assume the FINES vectors are mutually orthogonal with unit length. Let $\hat{F}_\Theta$ (a $K \times D_{\Theta_k}$ matrix) denote the set of the obtained $D_{\Theta_k}$ FINES vectors.
7. Search maxima of the following cost function:

$$J_{fi}(\vec{l},\vec{m}) = 1 - a^T(\vec{l},\vec{m})\hat{F}_{\Theta_k}\hat{F}_{\Theta_k}^T a(\vec{l},\vec{m})/\|a(\vec{l},\vec{m})\|^2\quad\text{(Equation G)}$$

over the selected region $\Theta_k$. In Equation G, $a(\vec{l},\vec{m})$ represents the combination of the gain matrix for given location $\vec{l}$, i.e., $G(\vec{l})$, and the unit orientation vector $\vec{m}$, and given by $$a(\vec{l},\vec{m}) = G(\vec{l}) \cdot \vec{m}.\quad\text{(Equation H)}$$

Instead of maximizing Equation G over dipole location $\vec{l}$ together with orientation $\vec{m}$, the peak searching can also be done over 3 location parameters only, by minimizing the following:

$$\lambda_{min}\{U_G^T \hat{F}_{\Theta_k}\hat{F}_{\Theta_k}^T U_G\},\quad\text{(Equation I)}$$

where $\lambda_{min}$ is the smallest eigenvalue of the bracketed item, and $U_G$ (a $K \times 3$ matrix) contains the first three normalized left singular vectors of $G(\vec{l})$.

8. Repeat steps 4-7 for other brain regions, and p minimum locations are the estimates of the p equivalent current dipoles' locations.

Example 2

A Subspace Approach to EEG Dipole Source Localization

An approach to EEG three-dimensional (3-D) dipole source localization using a non-recursive subspace algorithm called FINES is presented herein. In estimating source dipole locations, the present approach employs projections onto a subspace spanned by a small set of particular vectors (FINES vector set) in the estimated noise-only subspace instead of the entire estimated noise-only subspace in the case of classic MUSIC. The subspace spanned by this vector set is, in the sense of principal angle, closest to the subspace spanned by the array manifold associated with a particular brain region. By incorporating knowledge of the array manifold in identifying FINES vector sets in the estimated noise-only subspace for different brain regions, the present approach is able to estimate sources with enhanced accuracy and spatial resolution, thus enhancing the capability of resolving closely-spaced sources and reducing estimation errors.

The present computer simulations show, in EEG 3-D dipole source localization, that FINES can resolve two closely-spaced dipolar sources, and can accurately estimate source locations. FINES' can also effectively perform when the noise level is high and/or correlations among dipole sources exist.

Methods

Forward Model

Assume an array of K EEG electrodes sensing signals from p current dipole sources. Use $f(t_n)$ to denote the measurement vector ($K \times 1$), which is the collection of all K channels at the time $t_n$. Dipole sources are related to the measurement vector through gain matrix G that describes the transfer function from dipole signals to the scalp EEG measurements. The head volume conductor model is incorporated into G in the forward model. The general forward model can be described as $$f(t) = G(L)q(t) + n(t),\quad(1)$$

where $G(L)$ is the ($K \times 3p$) gain matrix. Each dipole is associated with 3 columns in G. L, a $3 \times p$ matrix, contains the dipole location vectors:

$$L = [\vec{l}_1, \ldots, \vec{l}_p]\text{ with }\vec{l}_i = [x_i, y_i, z_i]^T.\quad(2)$$

$q(t)$ (a $3p \times 1$ column vector) represents the composite of dipole moment vectors due to p current dipoles:

$$q(t) = \begin{bmatrix} \vec{q}_1(t) \\ \vdots \\ \vec{q}_p(t) \end{bmatrix}\text{ with }\vec{q}_i(t) = \begin{bmatrix} q_{x_i}(t) \\ q_{y_i}(t) \\ q_{z_i}(t) \end{bmatrix}.\quad(3)$$

The measurement noise $n(t)$, a $K \times 1$ column vector, is modeled as a spatially and temporally white Gaussian process with power $\sigma^2$. If noise is colored, this requirement can be achieved by prewhitening of the collected data.

Dipole source localization estimates the dipole location and other source parameters from given N time samples: $\{f(t_n); n=1, \ldots, N\}$. Note that each dipole is associated with 6 source parameters per time sample: 3 for dipole location and 3 for dipole moment. For fixed dipole location and N time samples, the model given by (1) contains $3p+3pN$ source parameters. In the case of fixed dipole location and orientation, the $i^{th}$ dipole moment vector can be expressed by $\vec{q}_i = \vec{m}_i s_i(t)$, where $\vec{m}_i$ denotes the unit orientation vector ($3 \times 1$) and $s_i(t)$ is a time varying scalar representing the $i^{th}$ dipole signal. The forward model (1) can then be written as $$f(t) = A(L,M)s(t) + n(t) + n(t),\quad(4)$$

where $s(t) = [s_1(t), \ldots, s_p(t)]^T$ and $A(L,M) = G(L)M$, with M a block diagonal matrix whose $i^{th}$ block is $\vec{m}_i$. In this Example, a fixed dipole location/orientation is assumed and forward model (4) is used.

Signal Subspace and Noise-Only Subspace

Besides the assumption of spatially and temporally white noise stated above, additional assumptions necessary for MUSIC-type algorithms to work appropriately are stated in Schmidt (1979) and Mosher et al. (1992). These assumptions include 1) time series from different sources are linearly independent, i.e., less than 100% mutually correlated; 2) the number of time samples (snapshots) is greater than the number of sensors, 3) the number of sources is smaller than the number of sensors, and 4) matrix A is of full rank, i.e., there is no array manifold ambiguity.

Using the model given by (4), $R_f(K \times K)$, the spatial correlation matrix of measurement f(t), can be expressed as $$R_f = A R_s A^T + \sigma^2 I, \quad (5)$$

where $R_s$ (p×p) is the correlation matrix of s(t), and I is the K×K identity matrix. The assumption 1) in the previous paragraph implies that $R_s$ is a full-rank matrix. If eigen-decomposition is applied to $R_f$ with the eigenvalues in nonincreasing order, the collection of the first p normalized eigenvectors is denoted as $E_s$, a (K×p) matrix, and the remaining normalized eigenvectors as $E_n$, a [(K×(K−p)] matrix. It should be noted that the assumptions in the previous paragraph imply that i) $R_s$ is not rank deficient and ii) that the first p eigenvalues are greater than the noise power $\sigma^2$ and each of the remaining (K−p) smallest eigenvalues is equal to $\sigma^2$. Therefore the range of $E_s$ is called the signal subspace and the range of $E_n$ is called the noise-only subspace. It is well known that the column space of A is the same as the signal subspace and is orthogonal to the noise-only subspace, as this is the property all subspace methods are based on.

Let $\hat{R}_f$ denote the sample correlation matrix of $R_f$, obtained by averaging the outer products of N time samples: $\{f(t_n); n=1, \ldots, N\}$, i.e., $$\hat{R}_f = \frac{1}{N} \sum_{n=1}^{N} f(n) f^T(n). \quad (6)$$

Suppose $\{\hat{\lambda}_i; i=1, 2, \ldots, K; \hat{\lambda}_i \geq \hat{\lambda}_{i+1}\}$ and $\{\hat{e}_i; i=1, 2, \ldots, K\}$ to be the ordered eigenvalues and corresponding normalized eigenvectors of $\hat{R}_f$. Assume that the number of dipoles has been determined. The estimates of $E_s$ and $E_n$ are obtained as follows:

$$\hat{E}_s = [\hat{e}_1, \hat{e}_2, \ldots, \hat{e}_p], \quad (7)$$

and $$\hat{E}_n = [\hat{e}_{p+1}, \hat{e}_{p+2}, \ldots, \hat{e}_K]. \quad (8)$$

In the MUSIC algorithm, the dipole location and orientation are obtained by employing projections onto the entire estimated noise-only subspace using the projection operator $\hat{E}_n \hat{E}_n^T$, i.e., finding the p peaks of the following cost function $$J_{mu}(\vec{l}, \vec{m}) = 1 - a^T(\vec{l}, \vec{m}) \hat{E}_n \hat{E}_n^T a(\vec{l}, \vec{m}) / \|a(\vec{l}, \vec{m})\|^2, \quad (9)$$

where $a(\vec{l}, \vec{m})$ is the combination of the gain matrix for given location $\vec{l}$ and the unit orientation vector $\vec{m}$, and given by $$a(\vec{l}, \vec{m}) = G(\vec{l}) \cdot \vec{m}. \quad (10)$$

Note that (9) only contains unknown source parameters associated with dipole source location and orientation; other unknown source parameters (e.g., source power, source correlation or time series of the concerned dipoles) and noise parameters do not appear in (9). Therefore there is a large computational saving compared to some other dipole source localization algorithms where all unknown parameters need to be solved simultaneously. To further reduce the computational load, the 3-dimensional location vector can be separated from the orientation vector in (9). Estimating dipole source locations becomes a task to find the p minimums of $$\lambda_{min}\{U_G^T \hat{E}_n \hat{E}_n^T U_G\} \quad (11)$$

with respect to $\vec{l}$, where $U_G(K \times 3)$ contains left singular vectors of $G(\vec{l})$, and $\lambda_{min}$ is the smallest eigenvalue of the bracketed item (a 3×3 matrix) (Mosher et al. 1992).

RAP-MUSIC is recursive, and the projection operator $\hat{E}_n \hat{E}_n^T$ and $a(\vec{l}, \vec{m})$ in (9) and (11) are replaced by different ones after the first recursion based on the estimate(s) of dipole location(s) from previous recursions (Mosher and Leahy 1999). Mathematically, the difference between classic MUSIC and RAP-MUSIC is that classic MUSIC uses projections onto the entire estimated noise-only subspace, and RAP-MUSIC does not in their $2^{nd}$ recursion and above. For example, in the 2nd recursion of RAP-MUSIC, i) the estimated noise-only subspace and $a(\vec{l}, \vec{m})$ are first projected onto $$\prod_{a(\hat{l}_1, \hat{\vec{m}}_1)}^{\perp} = I - \frac{a(\hat{l}_1, \hat{\vec{m}}_1) a^T(\hat{l}_1, \hat{\vec{m}}_1)}{\|a(\hat{l}_1, \hat{\vec{m}}_1)\|^2}, \quad (12)$$

where I is the identity matrix and $\{\vec{l}_1, \vec{m}_1\}$ are a dipole's location and orientation estimates from the first recursion; ii) a new projection operator is formed from $\pi_{a(\vec{l}_1, \vec{m}_1)}^{\perp} \hat{E}_n$ via re-orthogonalization (Golub and van Loan 1983), and iii) the new projection operator is used in the second recursion. Apparently, this newly formed projector for the $2^{nd}$ recursion is not $\hat{E}_n \hat{E}_n^T$.

The FINES Approach

In one example of FINES, the closeness criterion is the principal angle between two subspaces (see Golub and Van Loan (1983) for details on principal angles and vectors). FINES identifies a low-dimensional subspace (i.e., the FINES vector set that spans this low-dimensional subspace) in the estimated noise-only subspace that has the minimum principal angle to the subspace spanned by the section of the array manifold corresponding to a selected brain region. The array manifold represents a collection of the gain matrices when dipole location $\vec{l}$ varies over a selected region:

$$\Gamma = \{G(\vec{l}) | \vec{l} \in \Theta\}, \quad (13)$$

where $G(\vec{l})$ is the gain matrix (K×3) corresponding to three x, y, z unit-dipoles located at $\vec{l}$, and $\Theta$ represents the selected region. FINES employs this vector set to form a projection operator in searching dipole locations within the selected region. To search dipole locations over the entire brain, different sets of FINES vectors are used to form projection operators for different brain regions.

Figure 1B:
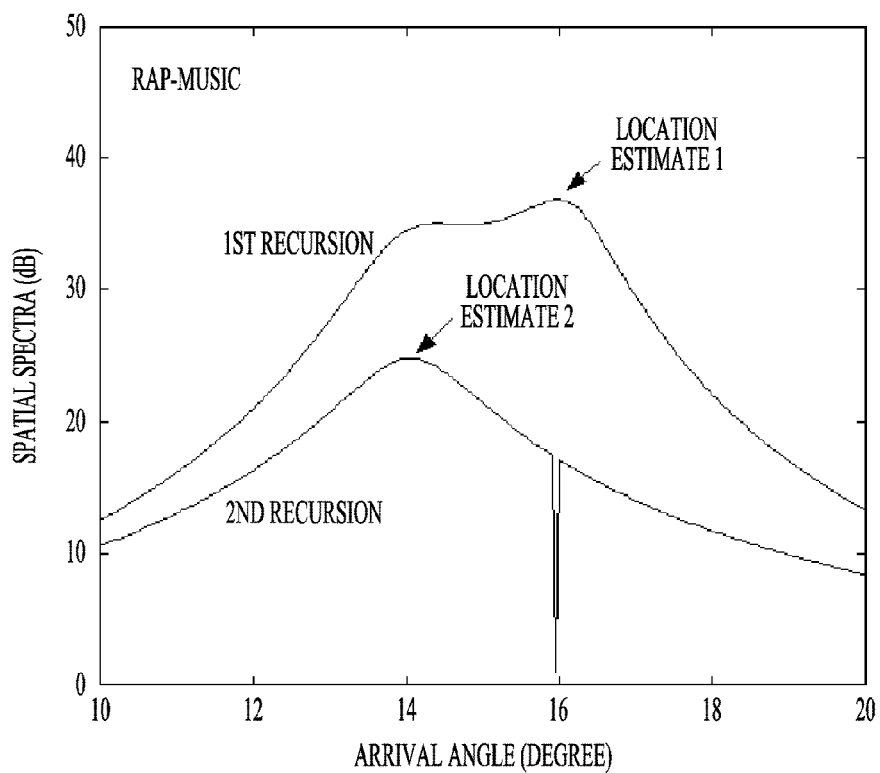

The rationale behind the FINES approach is that because the FINES vector set is algebraically closest to the array manifold for a specific region of interest in the brain, the approach is able to force down the values of the maximization cost function across the selected region while effectively pulling out source peaks. FIG. 1 illustrates a 1-D example: spatial spectra (i.e., cost function values) generated by FINES, MUSIC and RAP-MUSIC. The two sources arrive from 14 and 16 degrees, respectively. FIG. 1A demonstrates that while the MUSIC spectrum barely shows two peaks, FINES' spectrum displays two sharp peaks. Thus, the two source peaks are pulled out effectively by the FINES vectors. Therefore, using FINES, dipole locations can be estimated more easily and accurately, and the resolvability threshold is lower. RAP-MUSIC pulls out source peaks to be detected by suppressing source peaks that have been estimated already. In this 1-D example (see FIG. 1B), after the location of the source at 16° is estimated in the 1$^{st}$ recursion (i.e., using classic MUSIC), the second recursion employs a different projection operator so that the initial highest peak is suppressed dramatically. Thus, the other peak stands out, and can be estimated more easily and accurately.

Below, the FINES algorithms adapted for 3-D dipole source localization in EEG are described.

1. Divide the brain volume into a number of regions of similar volume. For example, the number of brain regions can be any number, for example, 16.

2. For the k$^{th}$ region $\Theta_k$, determine a subspace that essentially spans the array manifold corresponding to the region, i.e., $\{G(\vec{l}): \vec{l} \in \Theta_k\}$ where $\vec{l}=[x,y,z]^T$. This can be achieved through the following steps:

a. Form a spatially extended source representation matrix for the selected brain region $\Theta_k$:

$$R_{\Theta_k} = \int_{\Theta_k} w(\vec{l}) \cdot G(\vec{l}) G^T(\vec{l}) d\vec{l}, \quad (14)$$

where $w(\vec{l})$ is a weighting function that is optional and can include additional information about, e.g., head model or characteristics of the brain region to further enhance FINES' performance.

b. Perform an eigen-decomposition on $R_{\Theta_k}$ with eigen-values in nonincreasing order (i.e., the first eigenvalue is the largest and the last eigenvalue is the smallest). Because $R_{\Theta_k}$ is typically of low rank, there are only a few significant eigen-values.

c. Select the first $D_{\Theta_k}$ eigen-vectors that are associated with the $D_{\Theta_k}$ largest eigenvalues of $R_{\Theta_k}$ and form:

$$V_{\Theta_k} = [v_1, v_2, \ldots, v_{\Theta_k}]. \quad (15)$$

The dimension of $V_{\Theta_k}$ is important to the performance of FINES. To ensure that $V_{\Theta_k}$ adequately represents the array manifold corresponding to region $\Theta_k$ without sacrificing FINES' resolvability for localizing closely-space dipoles, use the eigenvalues of $R_{\Theta_k}$ to determine $D_{\Theta_k}$. Specifically, choose $D_{\Theta_k}$ such that the summation of the first $D_{\Theta_k}$ eigenvalues is not less than 99% of the summation of all eigenvalues. (Typically, $D_{\Theta_k}$ is in the range of 8-10 for an appropriate 128-electrode configuration.)

3. Repeat step 2 for all regions. It is important to note that for any given region $\Theta$ the corresponding $V_\Theta$ is independent of EEG measurements.

Therefore, for a given array configuration, all $V_\Theta$'s only need to be generated once and stored.

4. For given time samples of EEG measurement, form sample correlation matrix $\hat{R}_f$ as (Equation A).

5. By applying an eigen-decomposition to $\hat{R}_1$, generate the estimated noise-only subspace, i.e., the eigenvector matrix $\hat{E}_n$.

6. For the k$^{th}$ region $\Theta_k$, identify a set of $D_{\Theta_k}$ FINES vectors from the given $\hat{E}_n$, which is closest to the range of $V_{\Theta_k}$ in the sense of principal angle. This can be achieved through singular value decomposition (see Golub and Van Loan, 1983, pp. 428-429; and see Buckley and Xu, 1990). Assume the FINES vectors are mutually orthogonal with unit length. Let $\hat{F}_\Theta$ (a $K \times D_{\Theta_k}$ matrix) denote the set of the obtained $D_{\Theta_k}$ FINES vectors.

7. Search maxima of the following cost function:

$$J_{fi}(\vec{l},\vec{m}) = 1 - a^T(\vec{l},\vec{m}) \hat{F}_{\Theta_k} \hat{F}_{\Theta_k}^T a(\vec{l},\vec{m}) / \|a(\vec{l},\vec{m})\|^2, \quad (16)$$

over the selected region $\Theta_k$. Similar to MUSIC, instead of maximizing Equation G over dipole location $\vec{l}$ together with orientation $\vec{m}$, the peak searching can be done over 3 location parameters only, by minimizing the following:

$$\lambda_{min}\{U_G^T \hat{F}_{\Theta_k} \hat{F}_{\Theta_k}^T U_G\}, \quad (17)$$

where $\lambda_{min}$ is the smallest eigenvalue of the bracketed item.

8. Repeat steps 4-7 for other brain regions, and p minimum locations are the estimates of p dipoles' locations.

Once dipole locations are determined, other unknown source and noise parameters can be estimated subsequently. The unit orientation vector for the dipole with estimated location vector $\hat{l}_o$ can be obtained by solving the following generalized eigenvalue problem (Strang, 1988 at page 343; Mosher and Leahy, 1999):

$$\{G^T(\hat{l}_o) \hat{E}_n \hat{E}_n^T G(\hat{l}_o)\} \vec{m} = \lambda \{G^T(\hat{l}_o) G(\hat{l}_o)\} \vec{m}. \quad (18)$$

The estimate of the orientation vector for this dipole is the eigenvector corresponding to the smallest eigenvalue of (18). After the dipole's location and orientation are determined, its time series of the dipoles can then be obtained by, e.g., a least squares fitting. If the strength and correlation of the dipoles are desired, a procedure described in Schmidt (1979) can be applied.

Results

Computer simulations were used to evaluate the performance of FINES for EEG 3-D dipole source localization under various simulation conditions in terms of estimation accuracy and the resolvability of two closely-spaced dipole sources in comparison with MUSIC and RAP-MUSIC.

In the present simulation study, it was assumed that the head volume conductor can be represented by a 3-layer concentric sphere model with radius of 100 mm (Wang and He, 1998). A 128-electrode configuration was used, and all the electrodes were evenly distributed over the upper hemisphere. For FINES, the brain was divided into 16 regions with approximately equal volume. In particular, the brain as a hemisphere was first divided into 4 quadrants; then in each quadrant the brain region is further divided into 4 horizontal slices. The thickness of each slice is as follows: the first one: z=0-15 mm, the 2$^{nd}$ one: z=15-35 mm, the 3$^{rd}$ one: z=35-60 mm, and the 4$^{th}$ one is z=60-85 mm.

Figure 2:
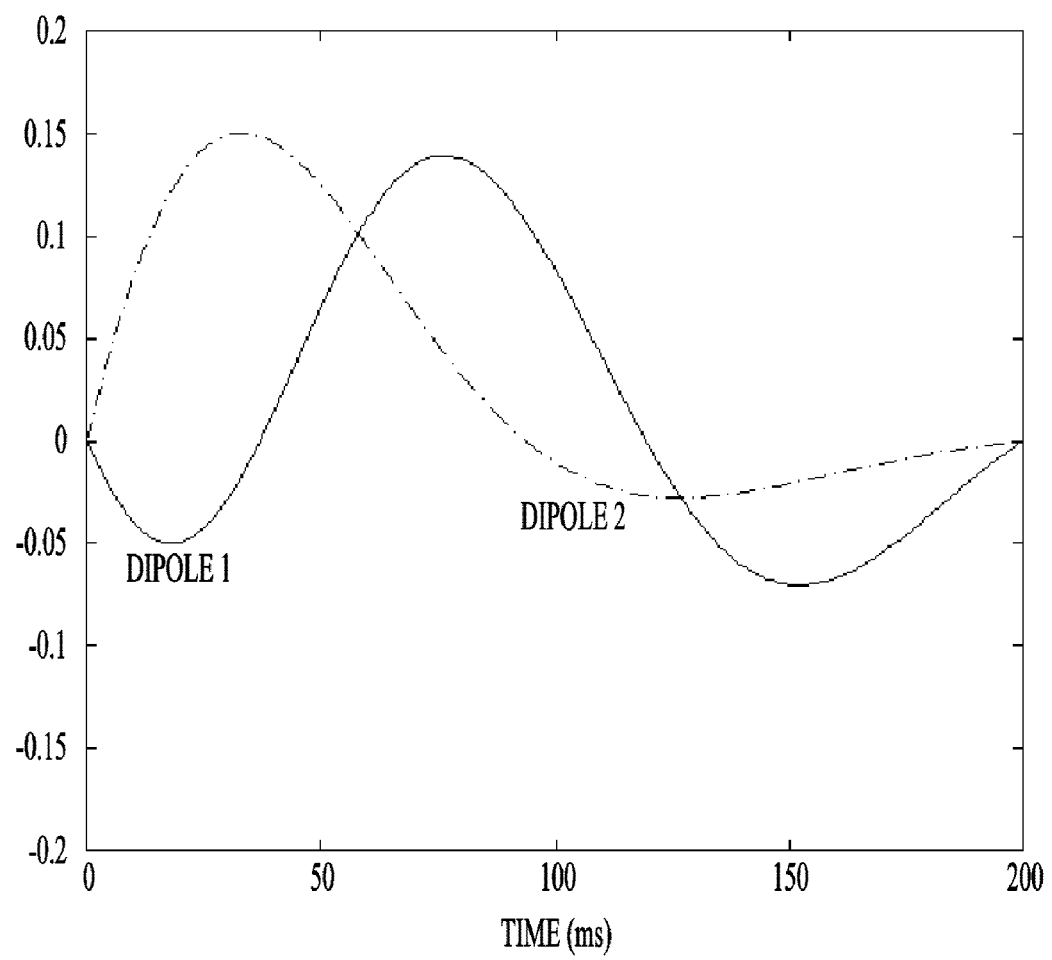
FIG. 2 depicts dipole waveforms used in simulation setting 1. The two dipoles were of equi-strength and correlated with $\rho=0.25$.

In simulation setting 1, two closely-spaced current dipoles of equal power were placed in the deep region of the brain: dipole 1 was located at $\vec{l}_1 = [13, 30, 20]$ (mm) and dipole 2 was at $\vec{l}_2 = [30, 13, 20]$ (mm). They were on the same z-plane 24 mm apart, and their eccentricities were the same: 38 mm. The waveforms of the two dipoles, shown in FIG. 2, were moderately correlated with $\rho = 0.25$, based on the definition of the source correlation below. Because (5) represents a correlation matrix rather than a covariance matrix, the correlation of two dipole waveforms is defined as follows:

$$\rho = \frac{\sum_{n=1}^{N} s_1(n) s_2(n)}{\sqrt{\sum_{n=1}^{N} s_1^2(n)} \sqrt{\sum_{n=1}^{N} s_2^2(n)}}, \quad (19)$$

where N represents the number of time samples. Equation (19) implies that when two time series are orthogonal (i.e., their inner product is zero), they are uncorrelated and $\rho$ is 0; when two time series are identical or only different by a scalar, they are completely correlated and ρ is 1. It is known that the three subspace methods addressed in this paper will fail when sources are fully correlated, i.e., ρ=1 because the source correlation matrix $R_s$ becomes rank-deficient. In this simulation setting, the EEG signals were sampled 200 times in the 200 ms interval corresponding to the dipoles' waveforms shown in FIG. 2.

With simulation setting 1, the performance of FINES was tested in two cases: the first case assumed radial orientation and the second one assumed tangential orientation.

FIG. 3, associated with case 1, displays mesh plots and 2-D images from the three algorithms, representing the reciprocal of their minimization cost functions at z=20 mm: for MUSIC, for FINES, and the one used in the $2^{nd}$ recursion for RAP-MUSIC (see Mosher and Leahy, 1999). More specifically, FIGS. 3A and 3B were obtained from a data set with SNR=10 dB, and FIGS. 3C and 3D were obtained from a data set with SNR=6 dB. Since for RAP-MUSIC, its first recursion is the same as classic MUSIC, only plots/images from its second recursion are shown. When SNR was 10 dB, all the three algorithms were able to provide dipole location estimates, while FINES showed sharper peaks. When SNR was 6 dB, MUSIC failed to resolve the two dipoles because it showed only one dull peak. On the other hand, both RAP-MUSIC and FINES were able to resolve two sources at such a low SNR (SNR of 6 dB is equivalent to noise level of 50% in amplitude). However, FINES provided more accurate location estimate for this data set. For RAP-MUSIC, the two dipole location estimates were [14.5, 27, 18.7] (mm) and [23, 16.7, 17.5] (mm) and thus the distance between the true and estimated dipole locations is 3.6 mm for dipole 1 and 8.3 mm for dipole 2. For FINES the two location estimates were [11.9, 28.8, 18.2] (mm) and [27.7, 13.3, 18.7] (mm), and thus the distance between the true and estimated dipole locations is 2.4 mm for dipole 1 and 2.7 mm for dipole 2.

In the second case, both dipoles' orientation were set to tangential. Table 1 shows statistics of the dipole location estimate errors in mm of the three algorithms based on 10 independent trials. The estimation error was defined as the distance between the true and estimated dipole locations. The dipoles' orientations were random for these 10 trials. In particular, they were tangential for all 10 trials but randomly changed from trial to trial while the angle between the two orientation vectors was kept at around 60 degrees. The white noise added was different in different trials and SNR was 10 dB. The averaged location errors for MUSIC, RAP-MUSIC, and FINES were 2.85 mm, 2.35 mm, and 2.25 mm, respectively. The standard deviations of the location estimation error for MUSIC, RAP-MUSIC, and FINES were 2.80 mm, 2.65 mm, and 0.95 mm, respectively. This simulation indicates that FINES outperformed MUSIC. Besides a reduction in error mean, FINES showed a significant reduction in error standard deviation, which indicates FINES' location estimates were more consistent. Additionally, the statistics on Table 1 also show FINES provided better results than RAP-MUSIC in terms of small variation of the localization estimation.

TABLE 1

Dipole location estimation errors: error mean and standard deviation (std) in mm (SNR = 10 dB, correlated sources with ρ = 0.25)

|  |  | dipole 1 $\vec{1}_1 = [13, 30, 20]$ | dipole 2 $\vec{1}_2 = [30, 13, 20]$ |
|---|---|---|---|
| MUSIC | error mean | 2.6 mm | 3.1 mm |
|  | error std | 3.2 mm | 2.4 mm |
| RAP-MUSIC | error mean | 1.8 mm | 2.9 mm |
|  | error std | 2.8 mm | 2.5 mm |
| FINES | error mean | 2.4 mm | 2.1 mm |
|  | error std | 0.9 mm | 1.0 mm |

In simulation setting 2, two closely-spaced current dipoles were placed in the shallow region of the brain. Dipole 1 was located at $\vec{1}_1=[8, 50, 50]$ (mm) and dipole 2 was at $\vec{1}_2=[20, 50, 50]$ (mm). They were on the same z-plane and only 12 mm apart, and their eccentricities were 71 mm and 73 mm, respectively, located in the cortex. The two dipoles were with radial orientation and of equal power. Like simulation setting 1, the EEG signals were sampled 200 times in a 200 ms internal.

In this simulation setting, SNR or the source correlation were varied to create a number of simulation conditions. 40 trials for each given simulation condition were run to reduce the fluctuation in performance assessment.

In this setting, besides error mean and standard deviation (std), the RMSE (Root Mean Squared Error) was also used to evaluate the location estimation accuracy, which is defined as:

$$RMSE(\hat{\vec{l}}_o) = \sqrt{\frac{1}{\#Trials}\sum_{i=1}^{\#Trials}\|\hat{\vec{l}}_o(i) - \vec{l}_o\|^2}, \quad (20)$$

where $\hat{\vec{l}}_o(i)$ denotes the estimate in the $i^{th}$ trial of dipole location vector $\vec{l}_o$. It is worthwhile to mention that the RMSE is an algebraic combination of the estimation error mean and standard deviation. Mathematically, their relationship is as follows:

$$(RMSE)^2 = (\text{error mean})^2 + (\text{error } std)^2. \quad (21)$$

Often RMSE is a simpler and more convenient measure to compare the performance of different algorithms, especially when error mean and standard deviation behave differently or a large amount of result needs to be compared. To evaluate resolvability, the following criterion were used: the two sources were considered resolved if there were two peaks located within 6 mm from the two true locations (Note: 6 mm is half the distance between the two true dipole locations). Additionally, in calculating the error mean/std and RMSE for RAP-MUSIC in this simulation setting, the location estimates from the $1^{st}$ recursion (the poorer one) were discarded, and only the results from the second recursion as Mosher and Leahy did in their original work (Mosher and Leahy 1999, Eq. 24) were used.

Table 2 shows error mean/std and RMSE of location estimation versus SNR using the three algorithms (two sources were uncorrelated: ρ=0). FINES consistently outperformed MUSIC for high and low SNR's. Further, MUSIC failed to reliably resolve two dipoles when SNR was low (at 14 or 12 dB) because it often generated only one dull peak or occasionally at least one peak was out of the defined searching region. Compared to RAP-MUSIC, FINES performed better when SNR was low, e.g., SNR=14, or 12 dB, while they performed similarly when SNR was high.

TABLE 2

Error mean, error std and RMSE, all in mm, of dipole location estimation of the three algorithms versus SNR for simulation setting 2 (the two dipoles were uncorrelated.)

| | | SNR | | | | | | | |
|---|---|---|---|---|---|---|---|---|---|
| | | 20 dB | | 16.5 dB | | 14 dB | | 12 dB | |
| | | dipole 1 | dipole 2 | dipole 1 | dipole 2 | dipole 1 | dipole 2 | dipole 1 | dipole 2 |
| MUSIC | Error mean | 0.7 | 0.6 | 1.7 | 1.5 | | | | |
| | Error std | 0.3 | 0.4 | 0.5 | 0.4 | — | — | — | — |
| | RMSE | 0.7 | 0.7 | 1.8 | 1.6 | | | | |
| RAP-MUSIC | Error mean | 0.3 | 0.3 | 0.4 | 0.5 | 1.0 | 1.4 | 2.8 | 2.4 |
| | Error std | 0.1 | 0.2 | 0.3 | 0.5 | 0.8 | 1.0 | 1.6 | 1.6 |
| | RMSE | 0.3 | 0.4 | 0.5 | 0.7 | 1.3 | 1.7 | 3.2 | 2.9 |
| FINES | Error mean | 0.4 | 0.4 | 0.7 | 0.8 | 0.8 | 1.2 | 1.4 | 1.3 |
| | Error std | 0.2 | 0.2 | 0.4 | 0.5 | 0.6 | 0.7 | 0.8 | 0.7 |
| | RMSE | 0.4 | 0.4 | 0.8 | 0.9 | 1.0 | 1.4 | 1.6 | 1.5 |

Table 3 shows error mean/std and RMSE of location estimation versus source correlation ρ (SNR was fixed at 16.5 dB). Again, FINES consistently outperformed MUSIC for both correlated and uncorrelated source cases, and MUSIC failed to reliably resolve two sources when ρ=0.25 or 0.50. Compared to RAP-MUSIC, FINES outperformed RAP-MUSIC when ρ=0.50.

TABLE 3

Error mean, error std and RMSE, all in mm, of dipole location estimation of the three algorithms versus source correlation ρ for simulation setting 2 (SNR = 16.5 dB, i.e., noise level in amplitude is 15% of the dipole signal)

| | | ρ | | | | | |
|---|---|---|---|---|---|---|---|
| | | ρ = 0 | | ρ = 0.25 | | ρ = 0.50 | |
| | | dipole 1 | dipole 2 | dipole 1 | dipole 2 | dipole 1 | dipole 2 |
| MUSIC | Error mean | 1.7 | 1.5 | | | | |
| | Error std | 0.5 | 0.4 | — | — | — | — |
| | RMSE | 1.8 | 1.6 | | | | |
| RAP-MUSIC | Error mean | 0.4 | 0.5 | 0.7 | 0.9 | 1.9 | 2.2 |
| | Error std | 0.3 | 0.5 | 0.6 | 1.1 | 1.8 | 1.9 |
| | RMSE | 0.5 | 0.7 | 0.9 | 1.4 | 2.6 | 2.9 |
| FINES | Error mean | 0.7 | 0.8 | 0.8 | 0.8 | 1.2 | 1.3 |
| | Error std | 0.4 | 0.5 | 0.5 | 0.4 | 0.7 | 0.7 |
| | RMSE | 0.8 | 0.9 | 0.9 | 0.9 | 1.4 | 1.5 |

In simulation setting 3, the resolvability as a function of dipole separation was studied, i.e., varying the distance between two dipoles while other parameters remained unchanged. Specifically, the distance between two dipoles varied from 8 mm to 20 mm while other parameters were fixed: the two dipoles were uncorrelated, of equal power and with radial orientation, SNR was at 16.5 dB (i.e., the noise level in amplitude was 15% of the dipole signal), and the EEG signals were sampled 200 times in a 200 ms interval. FIG. 4 shows mesh plots and 2-D images from the three algorithms, representing the reciprocal of their minimization cost functions at z=50 mm for 4 different cases:

Case 1: dipole 1 was located at [8, 50, 50] mm and dipole 2 was located at [16, 50, 50] mm; the dipole separation was 8 mm;

Case 2: dipole 1 was located at [8, 50, 50] mm and dipole 2 was located at [20, 50, 50] mm; the dipole separation was 12 mm;

Case 3: dipole 1 was located at [8, 50, 50] mm and dipole 2 was located at [24, 50, 50] mm; the dipole separation was 16 mm;

Case 4: dipole 1 was located at [8, 50, 50] mm and dipole 2 was located at [28, 50, 50] mm; the dipole separation was 20 mm.

Again, because the 1$^{st}$ recursion of RAP-MUSIC was identical to MUSIC, only plots/images from its second recursion are shown in FIG. 4.

When the dipole separation was only 8 mm, MUSIC failed to resolve the two dipoles while RAP-MUSIC and FINES were able to. When the dipole separation was 12 mm, 16 mm or 20 mm, all three algorithms were able to resolve two dipoles, but FINES shows sharper peaks. Therefore FINES had better source resolvability than MUSIC. In terms of estimation accuracy of dipole locations, FINES had better accuracy than RAP-MUSIC for case 1 when the dipole separation was only 8 mm, and for other 3 cases FINES and RAP-MUSIC had comparable estimation accuracy, for the trials given in FIG. 4.

Presented herein is an alternative subspace approach to 3-D dipole source localization. Its principle is based on projections onto a particular vector set in the noise-only subspace, which is, in the sense of principal angle, closest to the array manifold for a brain region of interest. The present computer simulations indicated that FINES provides better source resolvability and better estimation accuracy as compared with classic MUSIC, especially for localization of closed-spaced dipole sources. When SNR was low or sources were correlated, FINES also showed enhanced performance compared with RAP-MUSIC for the cases studied.

It is worthwhile to mention that steps 1-3 are independent of EEG measurement, i.e., dipole source and noise parameters. The representation subspace for a specific region only depends on the region and the electrode configuration. Therefore, all the representation subspaces $V_\Theta$'s for divided brain regions may be pre-generated and stored prior to the EEG measurement. Moreover, because $V_\Theta$'s are independent of EEG measurement, FINES does not need additional requirement on the number of time samples. In other words, its requirement on the number of time samples is the same as that for MUSIC: to successfully separate the signal subspace and noise-only subspace under various circumstances the number of time samples should be larger than the number of electrodes. Note that Tables 2 and 3 display location estimation errors that are significantly smaller than 7-8 mm observed in a recent study using a humans-skull phantom (Leahy et al., 1998). This thought to be because 1) in the present computer simulations no modeling errors or misspecification was assumed, 2) the algorithm used in the Leahy study for EEG dipole source localization was R-MUSIC, whose performance was poorer than RAP-MUSIC (Mosher and Leahy, 1999), 3) the present simulation study employed a 128-electrode configuration while Leahy et al. used a 64-electrode configuration in the experimental phantom study, and 4) the dipoles associated with the results on Table 2 and 3 were located in the shallow region of the brain.

The weighting function is an important factor in FINES, although it is optional. It can include, e.g., certain information about array configuration, brain regions and, may be made to be dependent of the orientation variable. With a carefully designed weighting function based on specific situations, the performance of FINES can be further improved. For example, the weighting on the shallow region may be different from the weighting on the deep region of the brain to enhance the detectability of deep sources.

Thus, FINES can be used for 3-D dipole source localization based on the performance of FINES for two dipole sources located in deep brain regions and cortical regions. The effects of noise level and source correlation on the FINES algorithm for localization of two dipole sources from scalp EEG was also assesed. These simulation results indicate that FINES is useful for localizing closely-spaced correlated sources under low SNR. This proposed subspace approach is also applicable to MEG dipole source localization.

Example 3

Reduced Spatially Correlated Noise Influence Using Subspace Source Localization Method FINES Described herein is a high resolution subspace approach for EEG source localization within a realistic geometry inhomogeneous head model. This approach reduces the influence caused by spatially correlated noise from background activities using FINES. Computer simulations were conducted on the realistic geometry head volume conductor model and compared with the MUSIC algorithm. The FINES approach was also applied to source localization of motor potentials induced by the execution of finger movement in a human subject. The present results indicate that FINES is insensitive to spatially correlated noise and has enhanced performance as compared with MUSIC.

In the motor potential analysis application, the realistic geometry boundary element head model, which consists of three conductivity boundaries between air and the scalp, the scalp and skull, and the skull and brain, were acquired and constructed from high-resolution T1-weighted 3D MRI images in a human subject. The conductivity ratio used for forward solution computation is 1:0.0125:1 for scalp:skull:brain (Rush et al., 1968; and Cuffin, 1990). Three conductivity boundaries were tessellated with high density vertices: 785 for the boundary between air and the scalp, 820 for the boundary between the scalp and skull and 1,042 for the boundary between the skull and brain. For simplicity, the computer simulations were also performed on this head model. The purpose of using the realistic geometry head model is to reduce the influence from co-registration error of generally applied approximated three-layer concentric sphere head model and evaluate the performance of FINES algorithm in a complex irregular shaped volume conductor.

Computer simulations were performed to evaluate the performance of FINES in a realistic geometry inhomogeneous head model, with reference to that of MUSIC under the influence of spatially correlated noise.

TABLE 4

|  | MUSIC (mm) | | | FINES (mm) | | |
| --- | --- | --- | --- | --- | --- | --- |
|  | 8 dB | 12 dB | 14.5 dB | 8 dB | 12 dB | 14.5 dB |
| Dipole 1 | 2.1763 | 1.0167 | 0.6478 | 1.2127 | 0.4046 | 0.4588 |
| Dipole 2 | — | 0.9463 | 0.2848 | 0.9666 | 0.4875 | 0.1698 |

Two uncorrelated current dipole sources were simulated at location (151, 187, 170) and (141, 197, 170). The values of the coordinates are confined to the boundary element head model constructed from MRI scans of the subject and expressed in millimeter. To generate the spatio-temporal distributed electrical field over the scalp, the radial oriented components of the current sources were modeled using exponentially damped sinusoidal functions. The Gaussian white noise was also added to make the final signal-to-noise ratio (SNR) equal to 8 dB. The simulated waveforms from 94 channels, which have same setup with experimental recordings explained below, are showed on the top in FIG. 5.

One extreme was detected from the MUSIC estimate which is showed in FIG. 5 (bottom, left) because of the significant influence from the spatially correlated noise. Two extrema could be detected from MUSIC estimator if pure Gaussian white noise was applied at the same level of SNR, which is not shown here. The location shift of the detected current dipole source could also be observed, which increased the estimation bias. Two extrema can be clearly identified from the FINES estimate in FIG. 5 (bottom, right). In order to explain the performance of two estimators, estimation biases at different levels of SNR are listed in Table 4.

Motor potentials induced by fast repetitive finger movement were recorded by a 96-channel EEG system. A right-handed normal subject took part in the present study.

The subject was instructed to perform fast repetitive finger movements which were cued by visual stimuli (Ni et al., 2003). 10-15 blocks of 2 Hz finger movements were recorded, with each 30 second blocks of movement and rest. EMG-locked averaging performed off-line. About 450 artifact-free single epochs were averaged according to the following procedure. The EEG data were digitally filtered with a band-pass of 0.3-50 Hz. Each EMG peak point was marked automatically using threshold detection. For averaging, single epoch from 200 ms before to 300 ms after EMG peak point were extracted from the continuous EEG data. The averaged 94-channel recordings are shown in FIG. 6 (top).

Two components in the time domain can be identified from multichannel waveforms. One arises from around −10 ms and ceases around 120 ms and is generated by execution of finger movement. The reconstructed current source is expected to be within the primary motor cortex (M1). Another component follows the previous one and has obvious waveform deviants from 110 ms to 250 ms which involves the event for planning next finger movement. This reconstructed current source is expected in the frontal premotor area or supplemental motor area (SMA). The overlapping of these two components in the time domain makes separation more difficult. Thus, in the problem of source location estimation for one component, the influence from the other one won't be avoided from data segment selection in the time domain. In this analysis, the data segment from −10 ms to 120 ms was used to estimate the area of brain activities which were induced by execution of finger movement to see the interference caused by planning for next movement.

Figure 6A:
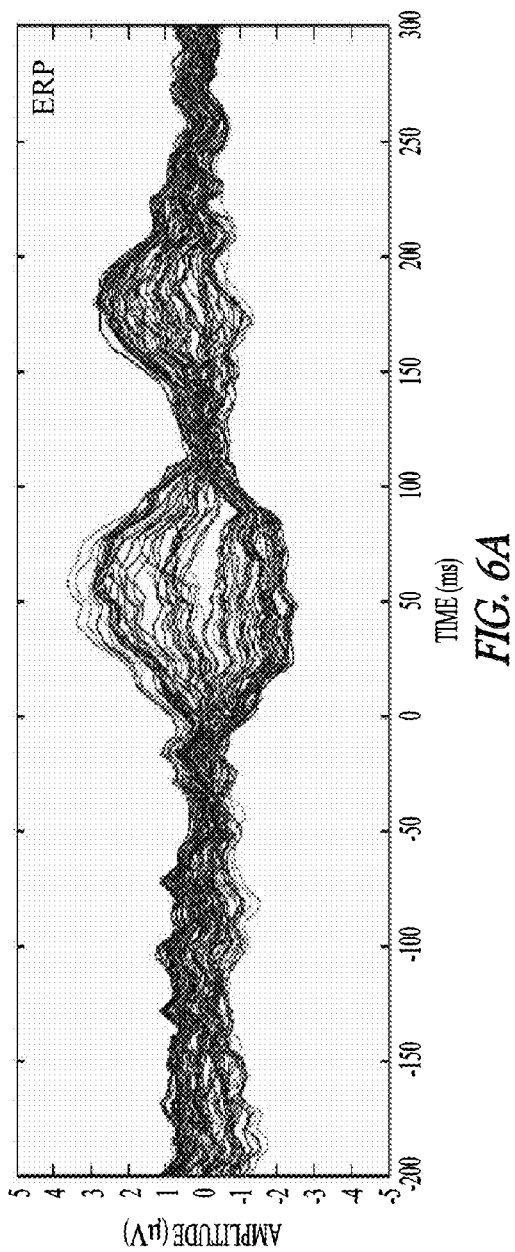
FIG. 6A). Axial view of MUSIC estimate at the plane where the extreme of activity is located (bottom, left.
Figure 6C:
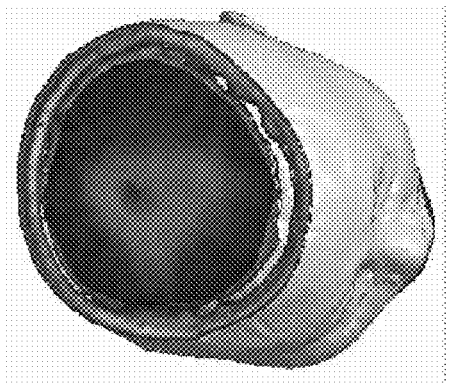
FIG. 6C). Note the enhanced spatial resolution of FINES.
Figure 6B:
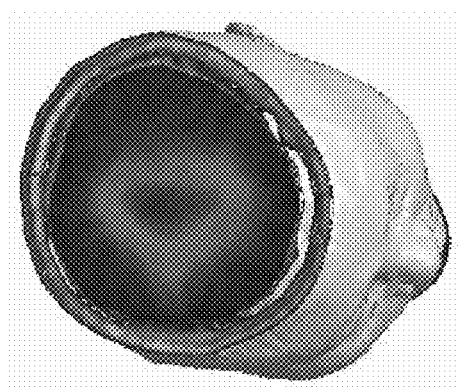
FIG. 6B). Axial view of FINES estimate at the plane where the extreme of activity is located (bottom, right.

The result of applying the MUSIC algorithm is shown in FIG. 6 (bottom, left) and the result from FINES algorithm is shown in FIG. 6 (bottom, right). The MUSIC estimate shows the distributed activities around the M1 and spreads to the frontal central area which is believed in the SMA. The extreme is still located in the M1 with a little shift to the front. The FINES estimate shows much more localized activated brain area exactly within the M1. Clearly, the interference caused by planning for next movement has a great influence in MUSIC on the estimate of motor potential source, which is generated by the execution of finger movement. FINES minimizes such interference using its size reduced noise subspace to perform the projection.

From the computer simulation and experimental study on motor potentials, the FINES estimate has shown improved spatial resolvability, less estimation bias, and robustness in source localization problems when the spatially correlated noise presents. Such cases are real situations which occur in practical problems such as motor potentials due to finger movement.

The definition of background noise depends on the research interest. In the motor potential analysis, localization of source generated by execution of finger movement is the primary interest. So the small contribution to the motor potential from planning in that selected data segment can be treated as background noise.

The simulation and experimental results presented herein indicate that FINES is insensitive to spatially correlated noise. Other methods introduced to reduce the effect of spatially correlated noise are mainly working on spatial covariance matrix of recordings, like in (Sekihara et al., 1997). The success of such methods depends on how accurately the noise covariance matrix is estimated. In most cases, accurate estimate of the noise covariance matrix is difficult. Furthermore, FINES algorithm can also be incorporated with such information if accurate noise covariance matrix can be estimated.

Example 4

The Use of FINES in Epilepsy Patients

In accordance with one embodiment, the dipole source distribution is localized from interictal and ictal data in epilepsy patients to predict and locate epileptogenic foci. For interictal spikes, a time window is selected covering the peaks of the interictal spikes and the FINES analysis is conducted to estimate the dipole source distribution. For ictal data, a time-frequency (TF) analysis can be performed to extract signals of interest and importance and FINES analysis performed. The goal of TF analysis is to give a description of the signal energy as a function of time and frequency. A good TF representation aids to extract features correctly and easily. Based on the uncertainty principle that the more precise the temporal localization, the more inaccurate the frequency information, and vice versa, a compromise between the time and frequency should be considered.

The ictal signal can be convoluted by complex Morlet's wavelets w(t,f):

$$w(t,f) = A \cdot \exp(-t^2/2\sigma_t^2)\exp(2i\pi ft) \quad (4.1)$$

with $\sigma_f = 1/2\pi\sigma_t$, $A = (\sigma_t\sqrt{\pi})^{-1/2}$.

A wavelet family is created by setting the trade-off ratio $(f/\sigma_f)$, the constant that determined the compromise between time and frequency localization, to an appropriate number. The wavelet family is then convolved to the signal at every frequency f and the square norm of the convolution is the time-varying energy [E(t,f)] of the signal at a specific frequency:

$$E(t,f) = \|w(t,f) \times s(t)\|^2 \quad (4.2)$$

Figure 8:
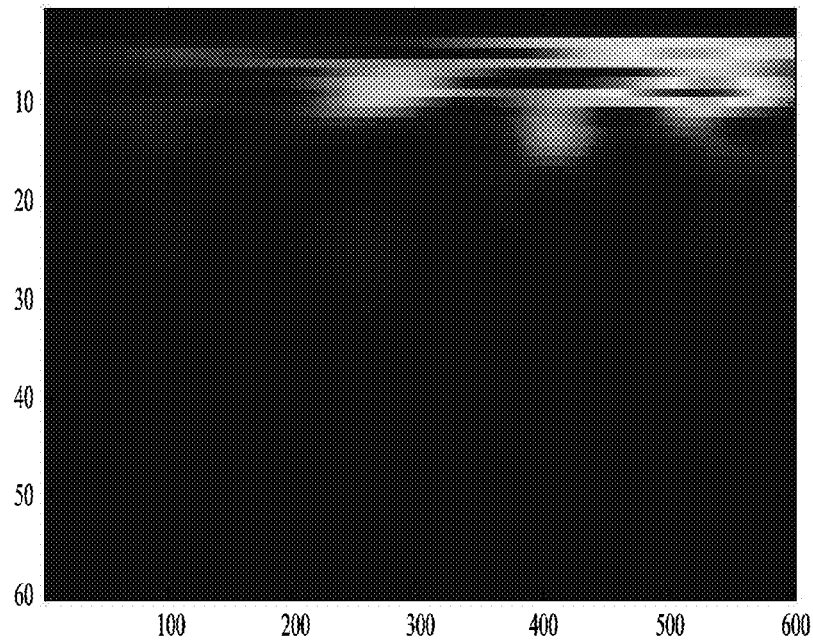
FIG. 8 depicts a time-frequency analysis of seizure data from a patient.
Figure 9A:
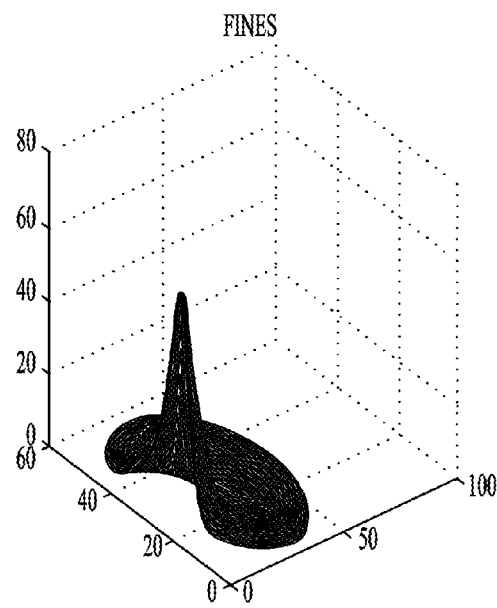
FIG. 9 (including FIGS. 9A and 9B) depicts FINES localization of an epileptic focus in a patient.
Figure 9B:
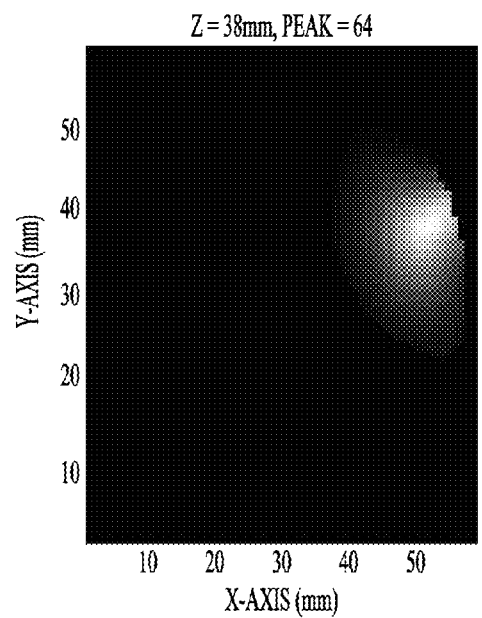

The time-frequency distribution (TFD) can be constructed by setting f from the lowest to the highest frequency that is of interest. As shown in FIG. 8, the horizontal axis refers to time and vertical refers to frequency. The value of the map represents the power of the signal at a specific time and frequency. FIG. 8 shows the T-F map of the ictal EEG at an electrode sensor in a patient of epilepsy. Based on the T-F analysis, the significant component of signal is extracted and FINES localization is conducted in this patient. Significant components include high energy concentrations or high energy. Energy level height is relative to surrounding energy concentrations. FIG. 9 shows one example of the FINES results. The left panel displays the source distribution at a cross-section of the brain and the vertical amplitude refers to the strength of the source distribution. The right panel displays the same source distribution but using a gray-scale representation. It is shown that the FINES shows sharp peak in the area corresponding to the epileptogenic foci as identified by single photon emission computerized tomography (SPECT), another medical imaging modality used to localize epilepsy.

Example 5

An Apparatus

Figure 7:
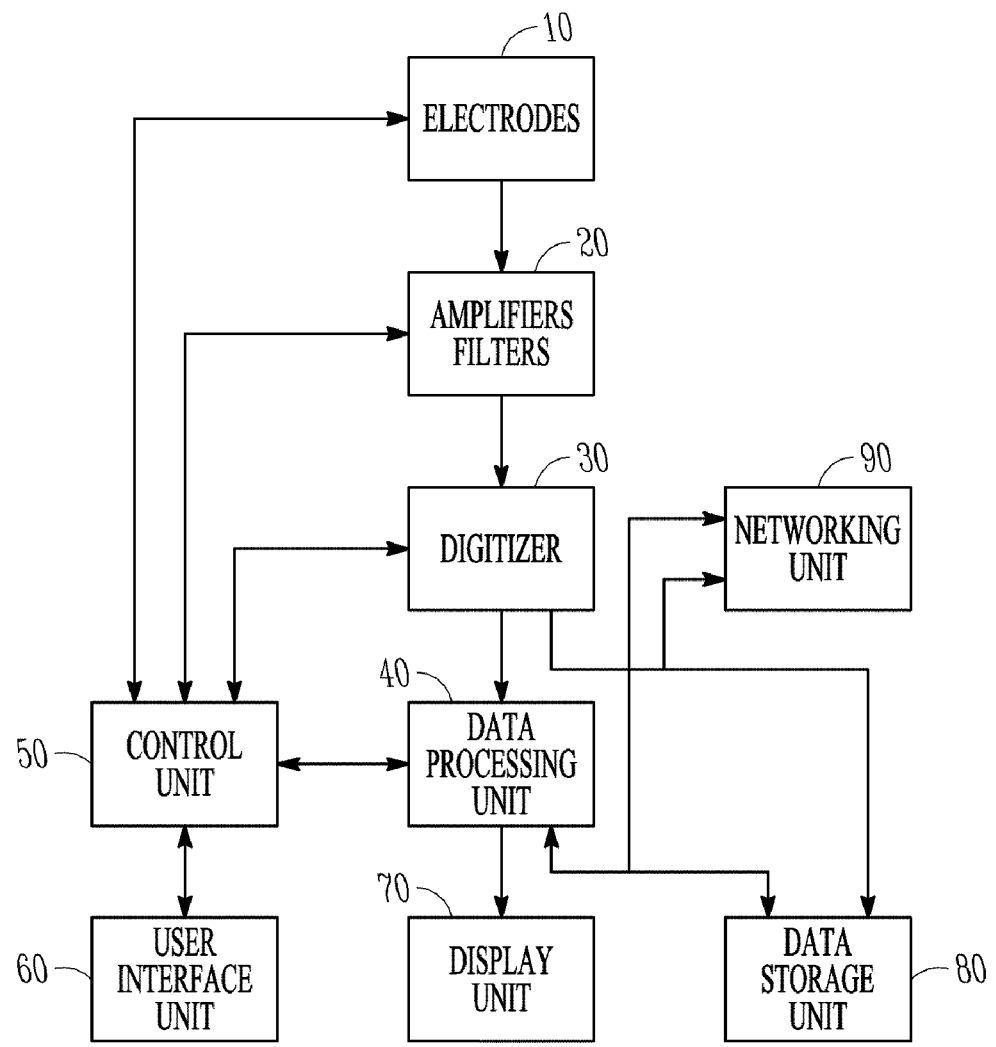
FIG. 7 depicts a block diagram of the functional blocks of an apparatus.

A general block diagram of an apparatus of one embodiment is shown in FIG. 7. The apparatus receives analog signals from electrodes 10, which have been attached to the scalp of the head of a person by methods known to the art worker. The number of electrodes can vary be from just a few to several hundreds. The locations of the electrodes attached to the scalp are recorded with respect to a coordinate system referenced to the person's head.

The received analog electrode signals are processed with amplifiers and filters 20 following methodology known to the art worker. After processing, the signals are digitized with a digitizer 30. The digitized data are then sent to data processing unit 40, where the FINES technique is employed to determine the locations of equivalent current dipoles in the brain. The results can be displayed, e.g., on a monitor or printer 70. The results, as well as the digitized original data, can be sent to the storage unit 80 and/or to another place through a networking unit 90. In the apparatus, there can be a user interface unit 60 and a control unit 50. The user interface unit 60 is for a human operator to interact with the apparatus. The control unit 50 is to synchronize the operation of the apparatus. Thus, the determination of the locations of equivalent current dipoles, i.e., neural sources in the brain, is carried out in the data processing unit 40 using the FINES technique.

DOCUMENTS CITED

Babiloni et al. *Electroenceph. & Clin. Neurophysoil* 102, 69-80 (1997).
Baillet et al., *IEEE Trans. Biomed. Eng.* 44, 374-385 (1997).
Buckley et al., *IEEE Trans. Acoust., Speech, Signal Processing* 38, 1842-1852 (1990).
Cooper et al., EEG Technology, $3^{rd}$ ed. Boston, Mass.: Butterworth (1980).
Cuffin, *IEEE Transactions on Biomedical Engineering.* 37 (1), 44-52 (1990).
Cuffin, *IEEE Trans. Biomed. Eng.* 43, 299-303 (1995).
Cuffin, *IEEE Trans Biomed. Eng* 42, 68-71 (1996).
Dale et al., *J. Cognitive Neuroscience* 5, 162-176 (1993).
Ding et al., "Reduced Spatially Correlated Noise Influence using Subspace Source Localization Method FINES", (In press).
Fuchs et al., *J. Clin. Neurophysiol.* 16, 267-295 (1999).
Gevins, *Electroenceph. Clin. Neurophysiol.* 106, 165-172 (1998).
Gevins et al., *Electroenceph. Clin. Neurophysiol.* 90, 337-358 (1994).
Golub et al., Matrix Computations Baltimore, Md.: John Hopkins University Press (1983).
Gorodnitsky et al., *Electroenceph. Clin. Neurophysiol.* 95, 231-251 (1995).
Hämäläinen et al., Interpreting measured magnetic fields of the brain: estimates of current distributions Tech. Rep. TKF-F-A559, Helsinki Uni. Of Technology (1984).
Hämäläinen et al., *IEEE Trans. Biomed. Eng.* 36:2, 165-171 (1989).
He et al., *IEEE Trans Biomed. Eng.* 34, 406-414 (1987).
He et al., *Medical and Biological Engineering and Computing* 30, 324-332 (1992).
He et al., *IEEE Trans Biomed Eng* 46, 1264-1268 (1999).
He et al., *Human Brain Mapping* 12, 120-130 (2001).
He et al., *Critical Reviews in Biomedical Engineering* 30, 283-307 (2002).
He et al., *NeuroImage* 16, 564-576 (2002).
Kosugi et al., *Neurological Research* 23, 435-446 (2001).
Leahy et al., *Electroenceph. Clin. Neurophysiol.* 107, 159-73 (1998).
Mosher et al., *IEEE Trans. Biomed. Eng.* 39, 541-557 (1992).
Mosher et al., *IEEE Trans. Signal Process.* 47, 332-340 (1999).
Ni Y, et al., "EEG Source Analysis of Motor Potentials Induced by Fast Repetitive Unilateral Finger Movement", *Proc. of IEEE EMBS International Conference on Neural Engineering* (2003).
Nunez et al., *Electroenceph. Clin. Neurophysiol.* 90, 40-57 (1994).
Pascual-Marqui et al., *Int. J. Psychophysiol.* 18, 49-65 (1994).
Rush et al., *Anesth Analg.* 47 (6), 717-723 (1968).
Salu et al., *IEEE Trans. Biomed. Eng.* 37, 699-705 (1990).
Scherg et al., *Electroenceph. Clin. Neurophysiol.* 62, 32-44 (1985).
Scherg, Fundamentals of dipole source potential analysis Auditory Evoked Magnetic Fields and Potentials Hoke M, Grandori F, Romani G editors Basel: Karger (1989).
Schmidt, Proc. Spectral Estimation Workshop, 243-258 (reprinted in 1986 in IEEE Trans. Antennas and Propagation 34, 276-280) (1979).
Sekihara et al., *IEEE Trans. Biomed. Eng.* 42, 149-157 (1995).
Sekihara et al., *IEEE Trans. Biomed. Eng.* 44:9, 839-847 (1997).
Sidman et al., *IEEE Trans Biomed Eng* 39, 437-444 (1992).
Strang, Linear Algebra and Its Applications $3^{rd}$ ed. International Thomson Publishing (1988).
Wang et al., *IEEE Trans Biomed. Eng.* 45, 724-735 (1998).
Wang et al., *IEEE Trans. Biomed. Eng.* 39, 665-675 (1992).
Wood, *Ann. NY Acad. Science* 388, 139-155 (1982).
Xu et al., *IEEE Trans. Signal Processing* 40, 2559-2569 (1992).
Xu et al., *Phys. Med. Biol.* 49, 327-343 (2004).
Xu et al., *IEEE Trans. Signal Processing* 42, 1812-1816 (1994).
Zhang et al., *Brain Topology* 7, 151-161 (1994).
U.S. Pat. No. 5,263,488
U.S. Pat. No. 5,687,724
U.S. Pat. No. 5,701,909
U.S. Pat. No. 6,330,470

While in the specification the subject matter has been described in relation to certain embodiments thereof, and many details have been set forth for purposes of illustration, it will be apparent to those skilled in the art that the subject matter is susceptible to additional embodiments and that certain of the details described herein may be varied considerably without departing from the basic principles.

All publications, patents and patent applications cited herein are herein incorporated by reference.

What is claimed is:

1. A processor implemented method comprising:
estimating a first subspace based on measured data for a brain;
calculating a second subspace, wherein the second subspace is orthogonal to the first subspace;
identifying a set of vectors of the second subspace, the vectors related to an array manifold associated with a selected region of the brain;
applying a projection onto the set of vectors; and
determining, using one or more processors, a location for each of at least one source based on a cost function of the projection for the selected region, and wherein the set of vectors have minimum principal angles to the array manifold.

2. The method of claim 1 further including calculating the array manifold based on a collection of gain matrices corresponding to the at least one source for the selected region, wherein the gain matrices are based on field responses corresponding to the measured data.

3. The method of claim 1 wherein applying the projection onto the set of vectors includes calculating a projection of an array response vector onto the second subspace, where the array response vector is a response to a unit dipole having a predetermined location and a predetermined orientation as measured by a sensor array about the brain.

4. The method of claim 1 wherein determining the location includes identifying a predetermined extrema of the cost function.

5. The method of claim 1 wherein estimating the first subspace includes processing at least one of electroencephalography data and magnetoencephalography data.

6. The method of claim 1 wherein estimating the first subspace includes receiving signals corresponding to electrical activity of the brain.

7. The method of claim 6 wherein receiving signals includes receiving signals from a plurality of sensors disposed about the brain.

8. The method of claim 7 wherein receiving signals from the plurality of sensors includes receiving location data for at least one of the plurality of sensors.

9. The method of claim 1 wherein the first subspace includes a signal-only subspace.

10. The method of claim 9 wherein the second subspace includes a noise-only subspace.

11. The method of claim 1 further including generating a three dimensional image depicting the location of each of the at least one source relative to the brain.

12. The method of claim 11 wherein generating the three dimensional image includes generating an image using at least one of magnetic resonance data, computerized tomography data, x-ray data and ultrasonic data.

13. The method of claim 1 further including generating at least one cross-sectional image or plot depicting the location for each of at least one source relative to the brain.

14. The method of claim 1 wherein the set of vectors spans the second subspace.

15. The method of claim 1 further including generating a sample spatial correlation matrix based on averaging outer products of a number of time samples and wherein the set of vectors includes a number of eigenvectors corresponding to eigenvalues of the sample spatial correlation matrix.

16. The method of claim 15 wherein the number of eigenvectors corresponds to a difference between a number of sensors and a number of dipole sources.

17. The method of claim 1 wherein calculating the second subspace includes using a second set of vectors corresponding to a number of largest eigenvalues of the sample spatial correlation matrix.

18. The method of claim 1 further including dividing the brain into a plurality of regions, and for each region of the brain, performing the estimating, calculating, identifying, applying, and determining.

19. The method of claim 1 wherein the second subspace is spanned by the array manifold corresponding to the selected region.

20. The method of claim 19 wherein the array manifold is formed by a collection of gain matrices, the gain matrices determined by field responses corresponding to a plurality of sensors about the brain and a dipole disposed in the selected region.

21. The method of claim 1 further including sampling electrical activity of the brain for a period of time to form the measured data.

22. The method of claim 21 further including forming a sample spatial correlation matrix using a particular set of time samples of the measured data.

23. The method of claim 22 wherein calculating the second subspace includes applying eigen-decomposition to the sample spatial correlation matrix.

24. The method of claim 1 wherein identifying the set of vectors includes determining proximity using the array manifold associated with the selected region.

25. The method of claim 1 wherein applying the projection includes forming projections for each of a plurality of array response vectors associated with a plurality of locations within the brain and having a plurality of orientations.

26. The method of claim 25 wherein determining the location includes identifying the location of at least one source based on searching the projections across a location vector and an orientation vector wherein the location corresponds to a first predetermined feature of the cost function.

27. The method of claim 26 further including identifying an orientation of the at least one source based on searching the projections across the location vector and the orientation vector wherein the orientation corresponds to a second predetermined feature of the cost function.

28. The method of claim 26 wherein the first predetermined feature includes at least one of a minima and a maxima of the cost function.

29. The method of claim 25 further including calculating the array response vectors based on at least one of a boundary element method, a finite element method and a finite difference method.

30. The method of claim 1 further including receiving the measured data and wherein the measured data includes at least one of magnetoencephalography data and electroencephalography data.

31. The method of claim 30 wherein receiving the measured data includes receiving data using a plurality of electrical electrode sensors disposed about the brain.

32. The method of claim 30 wherein receiving the measured data includes receiving data using a plurality of magnetic sensors disposed about the brain.

33. The method of claim 1 wherein identifying the set of vectors includes determining principal angles.

34. The method of claim 1 further including determining brain or head geometry using at least one of magnetic resonance and computer tomography.

35. The method of claim 1 wherein a time-frequency analysis is performed on the data to extract significant components.

* * * * *